United States Patent
Yang et al.

(10) Patent No.: US 11,351,308 B2
(45) Date of Patent: Jun. 7, 2022

(54) AUTO-INJECTOR WITH SIGNALING CAP

(71) Applicant: AMGEN INC., Thousand Oaks, CA (US)

(72) Inventors: Huaying Yang, Vernon Hills, IL (US); Desheng Yin, Thousand Oaks, CA (US); Ferry Tamtoro, San Ramon, CA (US); Scott Robert Gibson, Granada Hills, CA (US); Keith P. Kogler, Simi Valley, CA (US); Michael Friedman, Newbury Park, CA (US); Neal Johnston, Dallas, TX (US); Adam B. McCullough, Westlake Village, CA (US)

(73) Assignee: AMGEN INC., Thousand Oaks, CA (US)

( * ) Notice: Subject to any disclaimer, the term of this patent is extended or adjusted under 35 U.S.C. 154(b) by 834 days.

(21) Appl. No.: 15/775,630

(22) PCT Filed: Dec. 9, 2016

(86) PCT No.: PCT/US2016/065712
§ 371 (c)(1),
(2) Date: May 11, 2018

(87) PCT Pub. No.: WO2017/100501
PCT Pub. Date: Jun. 15, 2017

(65) Prior Publication Data
US 2018/0318526 A1    Nov. 8, 2018

Related U.S. Application Data

(60) Provisional application No. 62/265,142, filed on Dec. 9, 2015.

(51) Int. Cl.
*A61M 5/32*    (2006.01)
*A61M 5/50*    (2006.01)
(Continued)

(52) U.S. Cl.
CPC ........ *A61M 5/3202* (2013.01); *A61M 5/3204* (2013.01); *A61M 5/5086* (2013.01);
(Continued)

(58) Field of Classification Search
CPC .. A61M 5/3202; A61M 5/3205; A61M 5/321; A61M 5/3213; A61M 5/3243;
(Continued)

(56) References Cited

U.S. PATENT DOCUMENTS 7,540,858 B2 * 6/2009 DiBiasi ................. A61M 5/326
                                                            604/192
8,021,344 B2 * 9/2011 Edwards ............. A61M 5/3157
                                                            604/197
(Continued)

FOREIGN PATENT DOCUMENTS

EP          1095668 A1    5/2001
JP       2011-519712 A    7/2011
(Continued)

OTHER PUBLICATIONS

Japanese Patent Application No. 2018-521111, Notice of Rejection, dated Nov. 17, 2020.
(Continued)

*Primary Examiner* — Shefali D Patel
(74) *Attorney, Agent, or Firm* — Marshall, Gerstein & Borun LLP

(57) ABSTRACT

A drug delivery device includes a housing defining a shell, a drug delivery assembly at least partially disposed within the housing, a cap defining an opening and being adapted to at least partially cover an end of the housing, at least one electronic component, a power source which powers the at least one electronic component, and a switch assembly. The drug delivery assembly comprises a guard which engages an inner surface of the housing and is movable between a first
(Continued)

position, a second position, and a third position relative to the housing and is adapted to restrict external contact with a cannula. The switch assembly causes the power source to provide power to the at least one electronic component when the cap is removed from the housing, restrict the power source from providing power when the cap is coupled to the housing and the guard is in the first position, and cause the power source to provide power when the cap is coupled to the housing and the guard is in the third position.

15 Claims, 16 Drawing Sheets

(51) Int. Cl.
| | |
|---|---|
| G16H 40/67 | (2018.01) |
| G16H 20/17 | (2018.01) |
| A61K 39/00 | (2006.01) |
| A61M 5/24 | (2006.01) |
| C07K 16/00 | (2006.01) |
| C07K 14/52 | (2006.01) |
| C07K 14/535 | (2006.01) |
| A61M 5/14 | (2006.01) |
| C07K 14/47 | (2006.01) |
| A61M 5/31 | (2006.01) |
| G16H 40/63 | (2018.01) |
| A61M 5/44 | (2006.01) |
| A61K 38/17 | (2006.01) |
| A61K 38/19 | (2006.01) |
| A61M 5/20 | (2006.01) |
| C07K 14/705 | (2006.01) |
| C07K 16/28 | (2006.01) |
| C07K 16/40 | (2006.01) |

(52) U.S. Cl.
CPC ........ *A61K 38/1793* (2013.01); *A61K 38/193* (2013.01); *A61K 2039/57* (2013.01); *A61M 5/1413* (2013.01); *A61M 5/2033* (2013.01); *A61M 5/24* (2013.01); *A61M 5/2466* (2013.01); *A61M 5/326* (2013.01); *A61M 5/3243* (2013.01); *A61M 5/3286* (2013.01); *A61M 5/44* (2013.01); *A61M 2005/2086* (2013.01); *A61M 2005/3104* (2013.01); *A61M 2005/3267* (2013.01); *A61M 2205/13* (2013.01); *A61M 2205/14* (2013.01); *A61M 2205/3368* (2013.01); *A61M 2205/3553* (2013.01); *A61M 2205/3561* (2013.01); *A61M 2205/3584* (2013.01); *A61M 2205/36* (2013.01); *A61M 2205/3606* (2013.01); *A61M 2205/50* (2013.01); *A61M 2205/505* (2013.01); *A61M 2205/52* (2013.01); *A61M 2205/581* (2013.01); *A61M 2205/609* (2013.01); *A61M 2205/8206* (2013.01); *A61M 2205/8212* (2013.01); *C07K 14/47* (2013.01); *C07K 14/52* (2013.01); *C07K 14/535* (2013.01); *C07K 14/70578* (2013.01); *C07K 16/00* (2013.01); *C07K 16/2803* (2013.01); *C07K 16/40* (2013.01); *C07K 2317/31* (2013.01); *C07K 2319/30* (2013.01); *G16H 20/17* (2018.01); *G16H 40/63* (2018.01); *G16H 40/67* (2018.01)

(58) Field of Classification Search
CPC .............. A61M 5/3245; A61M 5/3269; A61M 5/3271; A61M 5/3272; A61M 5/5086; A61M 2005/3252; A61M 2205/50; A61M 2205/82; A61M 2205/8206; A61M 5/3204
See application file for complete search history.

(56) References Cited

U.S. PATENT DOCUMENTS

| | | | |
|---|---|---|---|
| 9,295,784 | B2 | 3/2016 | Eggert et al. |
| 2010/0022963 | A1 | 1/2010 | Edwards et al. |
| 2014/0094743 | A1 | 4/2014 | Bengtsson |
| 2015/0290396 | A1 | 10/2015 | Nagar et al. |

FOREIGN PATENT DOCUMENTS

| | | | | |
|---|---|---|---|---|
| JP | 2012-519028 | A | 8/2012 | |
| JP | 2013-530004 | A | 7/2013 | |
| JP | 2014-502888 | A | 2/2014 | |
| WO | WO-2009/140251 | A2 | 11/2009 | |
| WO | WO-2010/098927 | A1 | 9/2010 | |
| WO | WO-2010/098931 | A1 | 9/2010 | |
| WO | WO-2012/001493 | A2 | 1/2012 | |
| WO | WO-2012/085033 | A1 | 6/2012 | |
| WO | WO-2012145685 | A1 * | 10/2012 | .............. A61M 5/50 |
| WO | WO-2015187793 | A1 | 12/2015 | |
| WO | WO-2015187797 | A1 | 12/2015 | |
| WO | WO-2015187799 | A1 | 12/2015 | |
| WO | WO-2015187802 | A1 | 12/2015 | |
| WO | WO-2015187805 | A2 | 12/2015 | |
| WO | WO-2016062807 | A1 | 4/2016 | |

OTHER PUBLICATIONS

International Preliminary Report on Patentability and Written Opinion of PCT/US2016/065712, dated Jun. 12, 2018.
Written Opinion of the International Searching Authority and International Search Report for International Application No. PCT/US2016/065712, dated Apr. 4, 2017.

* cited by examiner

AUTO-INJECTOR WITH SIGNALING CAP

CROSS-REFERENCE TO RELATED APPLICATIONS

This is the United States national phase of International Patent Application No. PCT/US2016/065712, filed Dec. 9, 2016, which claims priority to U.S. Provisional Patent Application No. 62/265,142, filed Dec. 9, 2015, the entire contents of each of which are incorporated herein by reference.

BACKGROUND

The present disclosure generally concerns systems and methods for use with drug delivery devices and relating to the powering of electronics contained therein which assist patients and provide increased device functionality.

Drugs may be administered through the use of drug delivery devices, such as autoinjectors or on-body injectors or infusers. These devices may replace older delivery systems using a combination of a syringe and a vial of the drug or medicament, or a pre-filled syringe. Autoinjectors and on-body injectors may be used to automate the injection and delivery or administration process, thereby simplifying the process for certain patient groups or sub-groups for which use of the syringe/vial combination or pre-filled syringe systems would be disadvantageous, whether because of physiological or psychological impediments.

Even with the use of drug delivery devices, such as autoinjectors, patients may experience challenges during the initial use of the drug delivery device after they have been prescribed a drug that is delivered or administered through the use of one of these devices. For example, the user may be uncertain as to whether the medication inside the drug delivery device is the medication prescribed for them. Additionally, the user may be uncertain whether the medication has expired and/or whether the injection should be delayed after a drug delivery device has been removed from cold storage, such as in a refrigerator, and if the injection should be delayed, how long it should be delayed. The user may also be uncertain if the actions and their sequence correctly operate the drug delivery device. Even if the correct actions are performed in the correct sequence, the user may be uncertain the drug has been completely delivered, such that the injection is complete. Patients may have any number of additional concerns related to the administration of the drugs.

As a result of these and other uncertainties and concerns patients may have, systems and methods are often provided which include any number of electronic components capable of assisting with the drug administration process. For example, systems and their corresponding approaches may include any number of sensors or devices capable of monitoring the drug delivery device and/or the surrounding environment to determine whether the drug may be comfortably administered as well as communicate information to the user, healthcare providers, and other interested parties. Because of the use of any number of electronics, the device must be capable of providing power at a number of times before, during, and after the drug administration process. Portable power devices such as batteries may have a limited life and thus difficulties may arise when providing power to the delivery devices after extended durations. Further, these devices may potentially overheat sensitive equipment due to prolonged operation, and may damage the medicament when electronics are in operational states for prolonged periods of time.

As set forth in more detail below, the present disclosure describes a drug delivery system and approaches embodying advantageous alternatives to existing drug delivery device packaging that may address one or more of the above challenges or needs.

SUMMARY

According to one aspect of the disclosure, a drug delivery device includes a housing defining a shell, a drug delivery assembly at least partially disposed within the housing, a cap defining an opening and being adapted to at least partially cover an end of the drug delivery device housing, at least one electronic component, a power source which powers the at least one electronic component, and a switch assembly. The drug delivery assembly may comprise a guard which engages an inner surface of the housing and is movable between at least a first, a second, and a third position relative to the housing. The guard may be adapted to at least partially restrict external contact with a cannula to act as a safety device. The electronic component or components, the power source, and the switch assembly may each be at least partially disposed in the cap. In these examples, the switch assembly is adapted to cause the power source to provide power to the at least one electronic component when the cap is removed from the housing, restrict the power source from providing power to the at least one electronic component when the cap is coupled to the housing and the guard is in the first position, and cause the power source to provide power to the at least one electronic component when the cap is coupled to the housing and the guard is in the third position.

In some approaches, a signal cap for an autoinjector includes a cap body defining a cap shell, at least one electronic component at least partially disposed in the cap shell a power source at least partially disposed in the cap shell, a switch at least partially disposed in the cap shell, and a spring lever at least partially disposed in the cap shell. The switch is movable between an activated position and a deactivated position and is adapted to cause the power source to provide power to the at least one electronic component when in the activated position. At least a portion of the spring lever is movable between at least a first position and a second position. When the spring lever is in the first position, the spring lever urges the switch into the deactivated position thereby restricting the power source from powering the at least one electronic component. When the spring lever is in the second position, the spring lever urges the switch to occupy the activated position thereby causing the power source to provide power to the at least one electronic component.

In some forms, a signal cap for an autoinjector may include a cap body defining a cap shell, at least one electronic component at least partially disposed in the cap shell a power source at least partially disposed in the cap shell, a switch at least partially disposed in the cap shell, and a rotatable spring lever at least partially disposed in the cap shell. The switch is movable between an activated position and a deactivated position and is adapted to cause the power source to provide power to the at least one electronic component when in the activated position. The spring lever may include a first section, a second section extending from the first section at an angle which has a first length having a switch engagement region and a second length forming a substantially U-shaped section with the first length. The second length may receive a compression force from a first component of the autoinjector. The spring lever rotates between a first configuration when the first section contacts a second component of the autoinjector and a second configuration when the first section either contacts a third component of the autoinjector or is disposed within a void region of the autoinjector. When the spring lever is in the first configuration, the switch engagement region causes the switch to be positioned in the deactivated position. When the spring lever is in the second configuration, the switch engagement region causes the switch to be positioned in the activated position.

In some forms, a signal cap for an autoinjector may include a cap body defining a cap shell, at least one electronic component at least partially disposed in the cap shell a power source at least partially disposed in the cap shell, a switch at least partially disposed in the cap shell, and a spring lever at least partially disposed in the cap shell. The switch is movable between an activated position and a deactivated position and is adapted to cause the power source to provide power to the at least one electronic component when in the activated position. The spring lever may comprise a first portion forming a bend extending radially away from the cap body and a second portion having a switch engagement region. When the bend experiences a first force exerted by a first portion of the autoinjector, the switch engagement region causes the switch to be positioned in the deactivated position. When the bend experiences a second force exerted by one of a second portion of the autoinjector and a void region of the autoinjector, the switch engagement region causes the switch to be positioned in the activated position.

In some forms, a signal cap for an autoinjector may include a cap body defining a cap shell, at least one electronic component at least partially disposed in the cap shell a power source at least partially disposed in the cap shell, a switch at least partially disposed in the cap shell, and a spring lever at least partially disposed in the cap shell. The switch is movable between an activated position and a deactivated position and is adapted to cause the power source to provide power to the at least one electronic component when in the activated position. The spring lever may comprise a first component forming a bend extending radially away from the cap body and a second component positioned angled relative to the first portion. The second component may have a switch engagement region and also may have a pretension force applied thereto. In the first configuration, the first component contacts the second component to urge the switch engagement region away from the switch such that the switch is in the deactivated position. In the second configuration, the first component does not contact the second component thereby allowing the second component to move to a pretensioned state whereby the switch engagement region engages and urges the switch to the activated position.

BRIEF DESCRIPTION OF THE DRAWINGS

The above needs are at least partially met through provision of the autoinjector with a signalling cap described in the following detailed description, particularly when studied in conjunction with the drawings, wherein.

Figure 1:
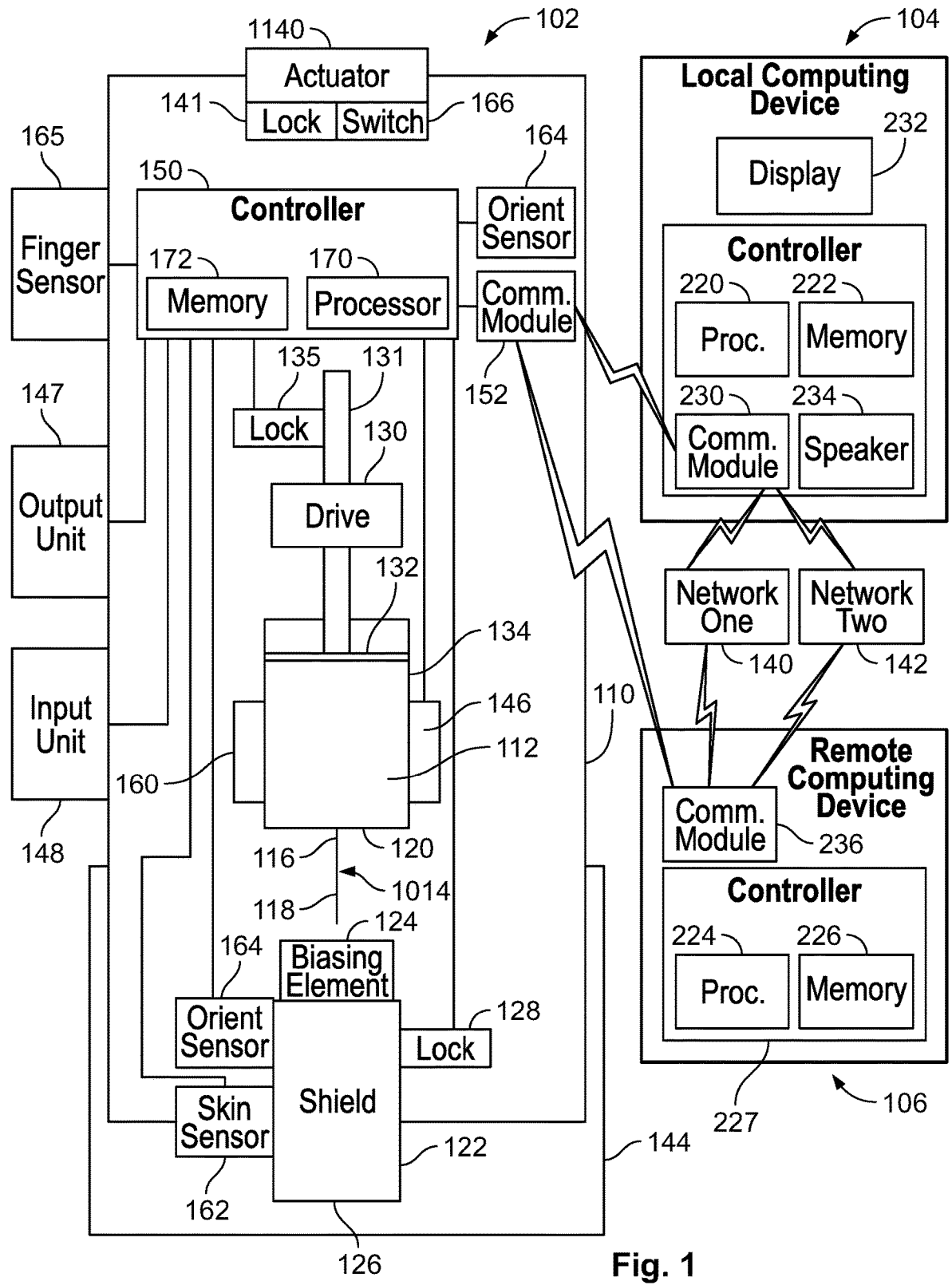
FIG. 1 comprises a schematic illustration of a system including a drug delivery device and a number of computing devices interconnected via a number of communication links and networks in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

This application is directed to a plurality of systems and approaches which include a drug delivery device and its corresponding system. In particular, the approaches described herein utilize removable a cap assembly which includes any number of electronic components used before, during, and/or after the drug administration process. The cap assembly includes a mechanism which activates a switch to provide power to the electronics based on the orientation of components of the drug delivery device. By way of example and not by any way of limitation, the mechanism may restrict the electronics from being powered when the cap assembly has not been removed and cause the electronics to be powered when the cap assembly has been removed from the device. Further, the mechanism may restrict the electronics from being powered when the cap assembly is recapped but the drug has not yet been administered and may cause the electronics to be powered when the cap assembly is recapped after the drug has been administered. In these examples, it is possible that a user may initially wish to administer the drug, but may change their mind and decide to delay the administering of the drug until a later time. As a result, the mechanism avoids unnecessary drainage of the battery when the device is in an idle, unused state, and may continue to perform as intended when the administering of the drug or drugs actually occurs.

Generally speaking, pursuant to these various embodiments, a drug delivery device includes a housing defining a shell, a drug delivery assembly at least partially disposed within the housing, a cap defining an opening and being adapted to at least partially cover an end of the drug delivery device housing, at least one electronic component, a power source which powers the at least one electronic component, and a switch assembly. The drug delivery assembly may comprise a guard which engages an inner surface of the housing and is movable between at least a first, a second, and a third position relative to the housing. The guard may be adapted to at least partially restrict external contact with a cannula to act as a safety device. The electronic component or components, the power source, and the switch assembly may each be at least partially disposed in the cap.

In these examples, the switch assembly is adapted to cause the power source to provide power to the at least one electronic component when the cap is removed from the housing, restrict the power source from providing power to the at least one electronic component when the cap is coupled to the housing and the guard is in the first position, and cause the power source to provide power to the at least one electronic component when the cap is coupled to the housing and the guard is in the third position.

The switch assembly may further include a switch being at least partially disposed in the cap shell and being movable between an activated position and a deactivated position and a spring lever at least partially disposed in the cap shell and may include a rigid portion and a resilient portion. The switch may be adapted to cause the power source to provide power to the at least one electronic component when in the activated position. At least a portion of the spring lever may be movable between at least a first position and a second position. When the cap assembly is coupled to the housing and the guard resides in the first position, a portion of the housing may contact the spring lever and move the spring lever into the first position. When the spring lever is in this first position, the spring lever urges the switch into the deactivated position. Further, when the cap assembly is coupled to the housing and the guard occupies the third position, the spring lever resides outside of the first position such that the switch occupies the activated position. Further still, when the cap assembly is removed from the housing, the spring lever is out of contact with the drug delivery assembly and occupies the second position such that the switch occupies the activated position. In some approaches, when the cap assembly is coupled to the housing and the guard occupies the third position, the spring lever is out of contact with the drug delivery assembly and occupies the second position such that the switch occupies the activated position.

In many of these forms, the housing may define at least one groove formed on an inner surface thereof. The guard may include at least one protrusion adapted to engage the at least one groove. The first, second, and third positions of the guard may correspond to a first, second, and a third stop of the at least one groove. It is understood that in some examples, the guard may define at least one groove formed on an outer surface thereof and the housing may define a protrusion which engages the groove. The groove may include a first section defining a first catch, a second section extending in a substantially axial direction, and a third section defining a second catch. At least a portion of the first section is angled relative to the second section.

The drug delivery assembly may further include a spring which exerts a force that causes the protrusion to engage the first catch. Upon exerting a compressive force on the spring, the protrusion is adapted to traverse the groove until the guard reaches the second position. Upon removing the compressive force on the spring, the protrusion is adapted to traverse the second section of the groove and engage the second catch.

The drug delivery device may further include a needle shield remover coupled to the cap assembly which is adapted to apply a biasing force to the resilient portion of the spring lever to urge the spring lever towards the second position. Further, the at least one electronic component is adapted to generate data representative of at least one of a condition and an operational state of the drug delivery device, the at least one electronic component further being adapted to transmit the data to a processing unit.

In some approaches, the spring lever is rotatable and comprises a first section, a second section extending from the first section at an angle. The second section may have a first length which includes a switch engagement region and a second length forming a substantially U-shaped section with the first length. The second length may receive a compression force from the needle shield remover. The spring lever rotates between the first configuration when the first section contacts the portion of the housing and the second configuration when the first section either contacts the guard or is disposed within a void region of the autoinjector.

In other approaches, the spring lever comprises a first portion forming a bend extending radially away from the housing and a second portion having a switch engagement region. When the bend experiences a first force exerted by a first portion of the autoinjector, the switch engagement region causes the switch to be positioned in the deactivated position. When the bend experiences a second force exerted by one of a second portion of the autoinjector and a void region of the autoinjector, the switch engagement region causes the switch to be positioned in the activated position.

In still other approaches, the spring lever may comprise a first component forming a bend extending radially away from the cap body and a second component positioned angled relative to the first portion. The second component may have a switch engagement region and having a pretension force applied thereto. In the first configuration, the first component contacts the second component to urge the switch engagement region away from the switch such that the switch is in the deactivated position. In the second configuration, the first component does not contact the second component thereby allowing the second component to move to a pretensioned state whereby the switch engagement region engages and urges the switch to the activated position.

Referring now to the drawings, and in particular to FIG. 1, one generalized example of a system 100 is provided which includes a drug delivery device 102, a local computing device 104 and a remote computing device 106. While the system 100 includes both a local computing device 104 and a remote computing device 106, not all embodiments according to this disclosure include both a local computing device 104 and a remote computing device 106.

The drug delivery device 102 may be in the form of an autoinjector, and thus is adapted for hand-held use and application against the skin of the patient. The drug delivery device 102 includes a housing 110 in which are disposed assemblies or structures that introduce a delivery cannula into the patient, and that eject a drug or medicament from a reservoir 112 through the delivery cannula into the patient. According to certain embodiments, the same assemblies or structures that introduce the delivery cannula into the patient may also eject the drug or medicament from the reservoir through the delivery cannula into the patient. The drug delivery device 102 may also include assemblies or structures that connect the delivery cannula to the reservoir, that withdraw the delivery cannula into the housing 110 through an opening in the housing 110 (not illustrated), or that deploy other structures that will prevent contact with the delivery cannula once the delivery cannula has been removed from the patient. Any number of additional assemblies and structures are possible. The specific embodiment of the drug delivery device 102 discussed below is thus by way of example and not by way of limitation.

Accordingly, the drug delivery device 102 includes a reservoir 112 and a delivery cannula 114 having a first end 116 (e.g., a proximal end) that may be connected or connectable in fluid communication with the reservoir 112 and a second end 118 (e.g., a distal end) that may be inserted into a patient. The delivery cannula 114 may be, for example, a rigid needle having a beveled edge that may be sized such that the second end 118 of the needle 114 is received under the skin so as to deliver a subcutaneous injection of the medicament within the reservoir 112. The first end 116 of the needle 114 may be disposed through a wall 120 of the reservoir 112, and thus be connected in fluid communication with the reservoir 112. Alternatively, the first end 116 of the needle 114 may be disposed only partially through the wall 120 (which wall 120 may be a resalable septum or stopper, for example) such that the first end of the needle 114 may not be connected in fluid communication until the second end 118 of the needle 114 is inserted into the patient. In such a circumstance, the first end 116 of the needle 114 may thus be described as connectable in fluid communication with the reservoir 112, although it will be recognized that there are other mechanisms by which the first end 116 of the needle 114 may be connectable, but not connected, in fluid communication with the reservoir 112.

The drug delivery device 102 includes a shield 122 (e.g., a needle shield) that may be deployed at least after the injection has been completed to limit access to the second end 118 of the needle 114. According to certain embodiments, the shield 122 may have a biasing element 124 (such as a spring) that extends the shield 122 from the housing 110 such that a distal end 126 of the shield 122 extends beyond the second end 118 of the needle 114 except when the shield 122 is disposed against the skin and the insertion of the needle 114 is actuated. In fact, the insertion of the needle 114 may be actuated according to certain embodiments of the drug delivery device 102 by disposing the distal end 126 of the shield 122 on or against the skin of the patient.

The drug delivery device 102 may also include a lock 128 (e.g., a ratchet) that is coupled to the shield 122 and configured to limit or prevent movement of the shield 122 relative to the housing 110 of the drug delivery device 102 such that the distal end 126 of the shield 122 extends from the housing 110 a sufficient distance to limit or prevent contact with the second end 118 of the needle 114, for example, after the needle 114 has been removed or separated from the skin of the patient. In some embodiments, the lock 128 may be coupled to a controller (e.g., controller 150 described in more detail below) which can selectively activate or deactivate the lock 128 based on different types of information regarding the drug delivery device 102, including operational state information, condition information, and/or identity information, in accordance with one or more of the methods described above. When the lock 128 is activated by the controller 150, the lock 128 may be configured to limit or prevent movement of the needle shield 122 relative to the housing 110. When the lock 128 is deactivated by the controller 150, the lock 128 may be configured to allow movement of the needle shield 122 relative to the housing 110.

The drug delivery device 102 also includes at least one drive 130 that may be used to insert the second end 118 of the needle 114 into the skin of the patient, and to eject the drug or medicament from the reservoir 112 through the delivery cannula 114 into the patient. The drive 130 may include one or more springs, according to certain embodiments. According to other embodiments, the drive 130 may include a source of pressurized gas or a source of a material that undergoes a phase change, such that the escaping gas or phase changing material provides a motive force that may be applied to the reservoir 112 to eject the drug therefrom. According to still other embodiments, the drive 130 may include an electromechanical system, such as may include a motor for example, although such an electromechanical system may be more appropriate for the on-body autoinjector or infuser described above. Other embodiments of the drive 130 are also possible.

In one embodiment, the drive 130 may be coupled to a plunger 131 and/or a stopper 132 (e.g., a wall) disposed in the reservoir 112 to move that stopper 132 in a distal direction toward the delivery cannula 114. In accordance with such an embodiment, the stopper 132 may be a stopper that is fixed to a distal end of the plunger 131 and received within a bore 134. The plunger 131, in conjunction with the drive 130, may move the stopper 132 along a longitudinal axis of the drug delivery device 102 through the bore 134 from a proximal end of the bore 134 to a distal end of the bore 134, and thereby eject the medicament from the reservoir 112.

In some embodiments, the drive 130 may also cooperate with the stopper 132 and/or the bore 134 to move the reservoir 112 relative to the housing 110 so as to move the second end 118 of the needle 114 relative to the housing 110 and into the patient. According to those embodiments wherein the drive 130 cooperates with the stopper 132, this may occur before the first end 116 of the needle 114 is in fluid communication with the reservoir 112. According to those embodiments wherein the drive cooperates with the bore 134, the drive may include one component (e.g., first spring) that cooperates with the bore 134 to move the reservoir 112 and needle 114 relative to the housing 110, and a second component (e.g., second spring) that cooperates with the stopper 132 to move the stopper 132 relative to the bore 134.

The drug delivery device 102 may also include a lock 135 that is coupled to the plunger 131 and configured to limit or prevent movement of the plunger 131 relative to the housing 110 of the drug delivery device 102 so that the stopper 132 cannot be advanced to discharge the medicament from the reservoir 112 to the patient. In some embodiments, the lock 135 may be coupled to a controller (e.g., controller 150 described in more detail below) which can selectively activate or deactivate the lock 135 based on different types of information regarding the drug delivery device 102, including operational state information, condition information, and/or identity information, in accordance with one or more of the methods described above. When the lock 135 is activated by the controller 150, the lock 135 may be configured to limit or prevent movement of the plunger 131 relative to the housing 110. When the lock 135 is deactivated by the controller 150, the lock 128 may be configured to allow movement of the plunger 131 relative to the housing 110.

The drive 110 may be associated with an actuator 140. The actuator 140 may activate the drive 130 to cause the drive 130 to insert the needle 114 and eject the drug from the reservoir 112 through the needle 114 into the patient. The actuator 140 may, according to certain embodiments, be the needle shield 122, as explained above. According to other embodiments, such as the one illustrated in FIG. 1, the actuator 140 may be a button that may be manually depressed by the user or patient once the drug delivery device 102 is placed disposed on or against the patient's skin. A lock 141 may be coupled to the actuator 140 and configured to limit or prevent movement of the actuator 140 so that the actuator 140 cannot be used to activate the drive 130. In some embodiments, the lock 141 may be coupled to a controller (e.g., controller 150 described in more detail below) which can selectively activate or deactivate the lock 141 based on different types of information regarding the drug delivery device 102, including operational state information, condition information, and/or identity information, in accordance with one or more of the methods described above. When the lock 141 is activated by the controller 150, the lock 141 may be configured to limit or prevent movement of the actuator 140 relative to the housing 110. When the lock 141 is deactivated by the controller 150, the lock 141 may be configured to allow movement of the actuator 140 relative to the housing 110.

The drug delivery device 102 may also include a removable sterile barrier or signal cap 144 that is disposed about one or more of a distal end of the housing 110, the needle shield 122, and the second end 118 of the delivery cannula 114. The signal cap 144 may be removably attached to the distal end of the housing 110 as shown in FIG. 1. In some embodiments, the signal cap 144 may form an interference or snap fit with the distal end of the housing 110. A frictional force associated with the interference or snap fit may be overcome by manually pulling the signal cap 144 in a direction away from a housing 110. The signal cap 144, when attached to the drug delivery device 102, may reduce the risk of contamination of the delivery cannula 114 and other elements disposed within the drug delivery device 102.

Additionally, the drug delivery device 102 may include a heating element 146 coupled to the exterior of the reservoir 112 and configured to warm the medicament inside the reservoir 112 through, for example, conductive heating. The heating element 146 may be coupled to the controller 150 so that the controller 150 can selectively activate or deactivate the heating element 146 based on different types of information regarding the drug delivery device 102, including operational state information, condition information, and/or identity information, in accordance with one or more of the methods described above. In some embodiments, the heating element 146 may include an electrically conductive coil that is wrapped around the exterior of the reservoir 112. In other embodiments, the heating element may include an electrically conductive coil wrapped around the cannula 114. Alternatively, or additionally, a cooling element (not illustrated) may be coupled to the reservoir 112 and controllable by the controller 150 in a manner similar to the heating element 146.

The drug delivery device 102 may also include an output unit 147 coupled to the housing 110 and configured to notify the patient or user of information related to the drug delivery device 102. The output unit 147 may be coupled to the controller 150 so that the controller 150 can selectively activate or deactivate the output unit 147 based on different types of information regarding the drug delivery device 102, including operational state information, condition information, and/or identity information, in accordance with one or more of the methods described above. The output unit 147 may be any device suitable for conveying information to the patient or user including a display (e.g., a liquid crystal display), a touchscreen, a light (e.g., a light emitting diode), a vibrator (e.g., an electro-mechanical vibrating element), a speaker, and/or an alarm, among other devices.

The drug delivery device 102 may also include an input unit 148 coupled to the housing 110 and configured to allow a user or patient to input information (e.g., password information) to be used by the controller 150. In some embodiments, the input unit 148, the output unit 147, and even the fingerprint sensor 165, may be a single device such as a touchscreen. In other embodiments, the input unit 148 may be a separate device from the output unit 147 such as a keyboard or button.

As illustrated in FIG. 1, the reservoir 112, the biasing element 124, the locks 128, 135, 141, the plunger 131, the stopper 132, and the drive 130, and the heating element 146 are disposed within the housing 110, along with at least part of the delivery cannula 114. Also disposed within the housing 110 is a controller 150, a communication module 152 (e.g., a wireless transmitter), and at least one sensor or switch. According to the embodiment illustrated in FIG. 1, four sensors are included: a temperature sensor 160, a skin sensor 162, at least one orientation sensor 164, and a fingerprint sensor 165. The sensors 160, 162, 164, and 165 may each generate sensor data (e.g., raw or unprocessed data) related to a respective measured property or aspect of the drug delivery device 102. The sensor data may be representative of at least one of a condition or operational state of the drug delivery device 102. Additionally, the drug delivery device 102 includes a switch 166. The controller 150 is coupled to the communication module 152, the locks 128, 135, 141, the sensors 160, 162, 164, 165, the heating element 146, the fingerprint sensor 165, the output unit 147, the input unit 148, and the switch 166. The controller 150 may be configured to process the sensor data generated by the sensors 160, 162, 164, and 165 to determine a condition and/or operational state of the drug delivery device 102. The controller 150, the communication module 152, one or more of the sensors 160, 162, 164, 165 and the switch 166 may be packaged together as a single module, or each component may be fabricated separately and coupled once the components are disposed within the housing 110. According to certain embodiments, each electrical component may be integrated into the structure of the device 102 associated with that electrical component (e.g., the sensors 162 and 164 may be integrated into the shield 122). In some embodiments, the controller 150, the communication module 152, one or more of the sensors 160, 162, 164, 165, and/or the switch 166 may be packaged together inside the signal cap 144.

The controller 150 may include at least one processor 170 (e.g., a microprocessor) and a memory 172 (e.g., a random access memory (RAM), a non-volatile memory such as a hard disk, a flash memory, a removable memory, a non-removable memory, etc.). The controller 150 may also include or be coupled to a power supply, e.g. a battery. The processor 170 may be programmed to carry out the actions that the controller 150 is adapted to perform and the memory 172 may include one or more tangible non-transitory readable memories having executable, computer-readable, non-transitory instructions stored thereon, which instructions when executed by the at least one processor 170 may cause the at least one processor 170 to carry out the actions that the controller 150 is adapted to perform. Alternatively, the controller 150 may include other circuitry that carries out the actions that the controller is adapted to perform.

The memory 172 may store the identity information discussed above. The identity information may be stored in the memory 172 prior to the start of execution of any of the methods discussed above. The identity information may include, by way of example and not by way of limitation, a unique identifier, the name of the drug, the dosage, an expiration date, and information regarding the identity of the patient for whom the drug was prescribed. With this information, the controller 150 or a local computing device (e.g., a smartphone) may make a determination regarding the patient that is about to receive the drug, and provide appropriate informational and/or instructional prompts. As an alternative to memory 172, the identity information may be contained in a QR code label or RFID tag associated with the drug delivery device 102.

The communication module 152 may be any of a number of different communication modules used to communicate with a local computing device (e.g., a smartphone) and/or a remote computing device (e.g., a server operated by the device manufacturer). According to one embodiment, the communication module 152 may be a Bluetooth and/or Bluetooth Low Energy module that is on-board with the controller 150. The communication module 152 is used to transmit information from the drug delivery device 102 to the local computing device 104 and/or the remote computing device 106. Alternatively, other wireless protocols, whether short range or long range, may be used by the communication module 152. Short range protocols may include for example radio-frequency identification (RFID), Zigbee, Wi-Fi, near field communication (NFC), and others, whereas long range protocols may include mobile telephony protocols, cellular, GSM, CDMA, LTE, WiMAX, EDGE, 3G, 4G, HSPA+, EV-DO, DECT, UMTS, iDEN, SMS messaging, satellite communication protocols, AMPS etc. In fact, the communication may be sent along a hardwired connection, rather than using the electromagnetic (EM) spectrum. As defined herein, a communication transmitted and/or received between the module 152, the local computing device, and/or the remote computing device may be in the form of a hardwired signal or EM signal or a pattern of such signals, for example.

The temperature sensor 160 may be disposed proximate to the reservoir 112 so that the temperature of the drug in the reservoir 112 may be determined. Alternatively, the temperature sensor 160 may simply be disposed in the housing 110, so that an approximate temperature of the drug in the reservoir 112 and of the drug delivery device 102 generally may be determined. According to an embodiment, the temperature sensor 160 may be an on-board temperature sensor 160 attached to the processor 170.

The skin sensor 162 may be attached to or associated with the shield 122 to determine when the drug delivery device 102 is disposed on or against the patient's skin. According to one embodiment, the skin sensor 162 is a pressure sensor.

According to other embodiments, the skin sensor 162 may be a capacitance sensor, resistance sensor, or inductance sensor. The skin sensor 162 or the switch 166 (which is attached to or associated with the actuator 140) may be used to determine when the drug delivery device 102 is activated or actuated, depending on the design and operation of the drug delivery device 102 that is used to actuate the drive 130, in accordance with the discussion above. It may also be the case that a signal from the skin sensor 160 is used to determine that the drug delivery device 102 has been activated even when the shield 122 is not used as the actual actuator, the underlying assumption being that the movement of the shield 122 is necessarily related to the actuation of the device 102.

The orientation sensors 164, of which there may be at least two as illustrated, may be associated with the shield 122 (or that portion of the housing 110 adjacent the shield 122) and the controller 150 (which may be, as illustrated, disposed at the other end of the drug delivery device 102 or the housing 110 from the shield 122). The orientation sensors 164 may be magnetometers, for example. In particular, the orientation sensor 164 associated with the controller 150 may be an on-board magnetometer. The orientation sensors 164 may be used to determine the orientation of the drug delivery device 102 (in particular, the housing 110) relative to the injection site (or more particularly, relative to the placement of the drug delivery device 102 on or against the patient's skin).

It will be recognized that the arrangement of the components of the drug delivery device 102 within the housing 110 is but one embodiment of this disclosure. For example, certain components of the drug delivery device 102 may be disposed outside the drug delivery device 102.

According to this embodiment, the drug delivery device 102 may include the housing 110, the reservoir 112, the needle 114, the shield 122, the biasing element 124, the lock 128, the drive 130, and the button 140. Furthermore, the sensors 162, 164 and the switch 166 may be disposed within the housing 110. The fingerprint sensor 165, the output unit 147, and the input unit 148 may be disposed on the exterior of the module 130 so that a user or patient can interact with them.

The separation of the controller 150, communication module 152 and other components into a module may permit the module to be used with multiple instances of the drug delivery device 102. In this regard, the module may be considered to be the reusable portion of the drug delivery device 102/module combination (which may be referred to as the drug delivery device 102 for purposes of this disclosure), while the drug delivery device 102 may be considered to be the disposable portion of the drug delivery device 102. By isolating the more expensive components into the reusable module 400 and the less expensive components (including certain sensors) into the disposable drug delivery device 102, the overall cost of the autoinjector may be optimized. This arrangement of the components in the module and the drug delivery device 102 may also facilitate the manufacture and sterilization of the drug delivery device 102 and module.

The local computing device 104 may be in the form of at least one computing device including at least one processor 220 (e.g., microprocessor) and a memory 222 (e.g., a random access memory (RAM), a non-volatile memory such as a hard disk, a flash memory, a removable memory, a non-removable memory, etc.). The at least one processor 220 and the memory 222 may be incorporated into a controller 223 of the local computing device 104 and/or may be configured separately. Likewise, the remote computing device 106 may be in the form of at least one computing device including at least one processor 224 (e.g., microprocessor) and memory 426 (e.g., a random access memory (RAM), a non-volatile memory such as a hard disk, a flash memory, a removable memory, a non-removable memory, etc.). The at least one processor 224 and the memory 226 may be incorporated into a controller 227 of the local computing device 104 and/or may be configured separately. The memories 222, 226 may include one or more tangible non-transitory computer-readable memories having computer-executable instructions stored thereon (for example, in the form of a custom Mobile Application, or an App for short, or other software module).

According to the illustrated embodiment, the local computing device 104 is a mobile computing device (e.g., a smartphone, smart watch, tablet computer, etc.) while the remote computing device 106 is a server. In some embodiments, the local computing device 104 can include generally any computing device capable of processing data and being synched to and in communication with the drug delivery device 102 such as, for example, a smart wearable device, a personal computer, a laptop computer, a smart television, a smart appliance, a smart automobile, a networked computer, etc. According to other embodiments, the local computing device 104 may be a dedicated device such as a hub or gateway that can establish a communication link with the communication module 152 and potentially the remote computing device 106, where communication with the remote computing device 106 is necessary or desirable.

The local computing device 104 may further include a communication module 230 for wireless communication with the communication module 152 of the drug delivery device 102, for example by using Bluetooth/Bluetooth Low Energy protocol. Alternatively, other wireless protocols may be used by the communication module 152, such as radio-frequency identification (RFID), Zigbee, Wi-Fi, near field communication (NFC), cellular, and others. The local computing device 104 may also include a display 232 to be used to communicate instructions to the user. The local computing device 104 may include other output devices other than the display 232 to communicate with the user, such as a speaker 234 for example. The speaker 234 may be controlled by the processor(s) 220 to provide an audible form of the instructions displayed in written form on the display 232.

The local computing device 104 may also include one or more communication modules, which may be the same as or different from the communication module 230, that may be used to communicate with one or more networks 240, 242. For example, the network 240 may be a wireless radio frequency network, such as a cellular mobile device network, while the network 242 may be a network of computing devices, such as the Internet. The networks 240, 242 may be in communication with each other, such that the local computing device 104 may communicate with the remote computing device 106 over the network 240, the network 242 or a combination of the networks 240, 242. The remote computing device 224 may include a communication module 236 to receive communications from the networks 240, 242.

While the terms "local" and "remote" have been used to describe the local computing device 104 and the remote computing device 106, these terms have not been selected to require a particular spatial or geographical distance between the devices 104, 106. Instead, the terms have been used to suggest a relative proximity to the user, and the fact that the remote computing device 106 is not required to be at the same physical location as the user and the drug delivery device 102. According to certain embodiments, it is possible, even likely, that the remote computing device 106 may be located in a different geographic location than the user and the drug delivery device 102, for example a different city, state or country.

The local computing device 104 and the remote computing device 106 are each separate from, and spaced apart from, the drug delivery device 102 and therefore may each be considered to be an "external computing device" relative to the drug delivery device 102.

Turning to FIGS. 2-5, a drug delivery device 10 is provided. The drug delivery device 10 may be in the form of an autoinjector, and thus configured for hand-held use and application against the skin of the patient. The drug delivery device 10 may include some or all of the same components as the drug delivery device 102 described above in connection with FIG. 1. The drug delivery device 10 may include a housing 11 which defines a shell in which are disposed assemblies or structures such as a drug delivery assembly which introduce a delivery cannula into a patient and that eject a drug or medicament from a reservoir through the delivery cannula into the patient. The drug delivery device 10 may also include an actuator disposed at a proximal end of the housing 11 and configured to be depressed by the patient to activate a drive to that causes a plunger to discharge the medicament from the reservoir through the delivery cannula into the patient.

Figure 5A:
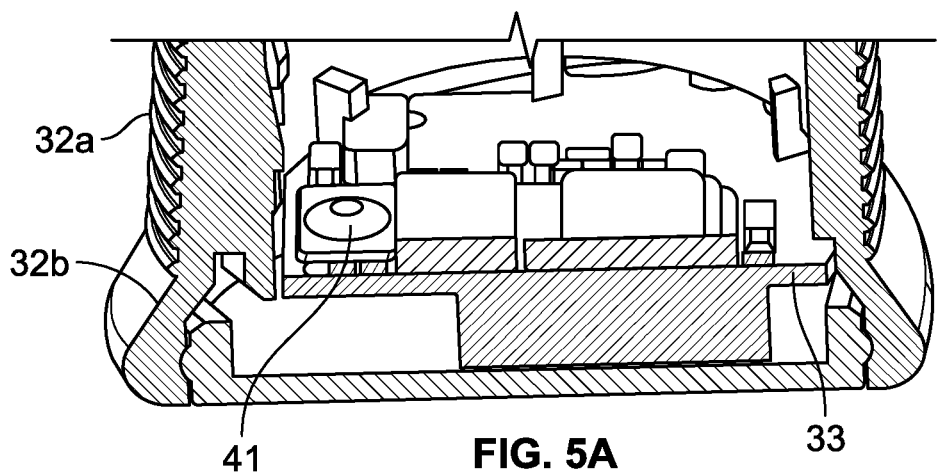
FIGS. 5A and 5B comprise a cross-sectional view of a cap assembly for an autoinjector, with FIG. 5A illustrating a switch disposed on an upper surface of an electronics module, and FIG. 5B illustrating the switch being disposed on a lower surface of the electronics module in accordance with various embodiments of the invention.
Figure 5B:
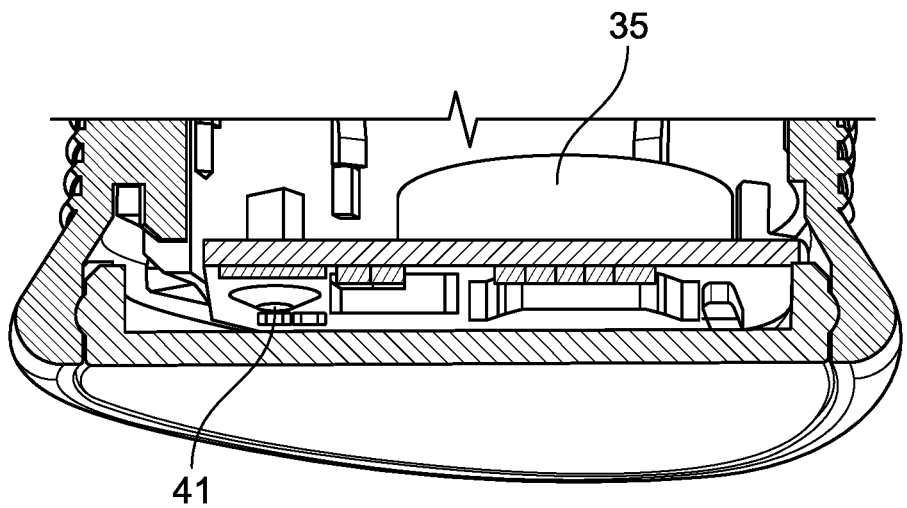

The drug delivery device 10 may further include a signal cap 30 removably attached to a distal end of the housing 11. The drug delivery device 10 may also include an electronic component 33, a power source 35 as illustrated in FIG. 5B, and a switch assembly 40, each of which may be at least partially disposed in the signal cap 30. The power source 35 is used to selectively power the electronic component 33. It is understood that any number of electronic components 33 may be used, and may include any combination of components previously stated with regards to FIG. 1. For example, the controller 150, the memory 172, the processor 170, the communication module 152 (e.g., a Bluetooth module, a Bluetooth Low Energy module, etc.), the skin sensor 162, the orientation sensor 164, the fingerprint sensor 165, the temperature sensor 160, the output unit 147, and/or the input unit 148 may be housed (e.g., embedded) within the signal cap 30. The electronic component 33 may generate data representative of at least one of a condition and an operational state of the drug delivery device and may further transmit that data to a processing unit.

The signal cap 30 may also serve as a removable sterile barrier which reduces the risk of contamination of the delivery cannula and other elements within the housing 11 prior to use of the drug delivery device 10. The signal cap 30 may be formed by a tubular member 32 and a cover member 31 that covers an open end of the tubular member 32. In some examples, the tubular member 32 and the cover member 31 may be integrally formed as a single unitary structure, or alternatively, formed as separate components which are adhered or mechanically interconnected to each other.

Figure 3:
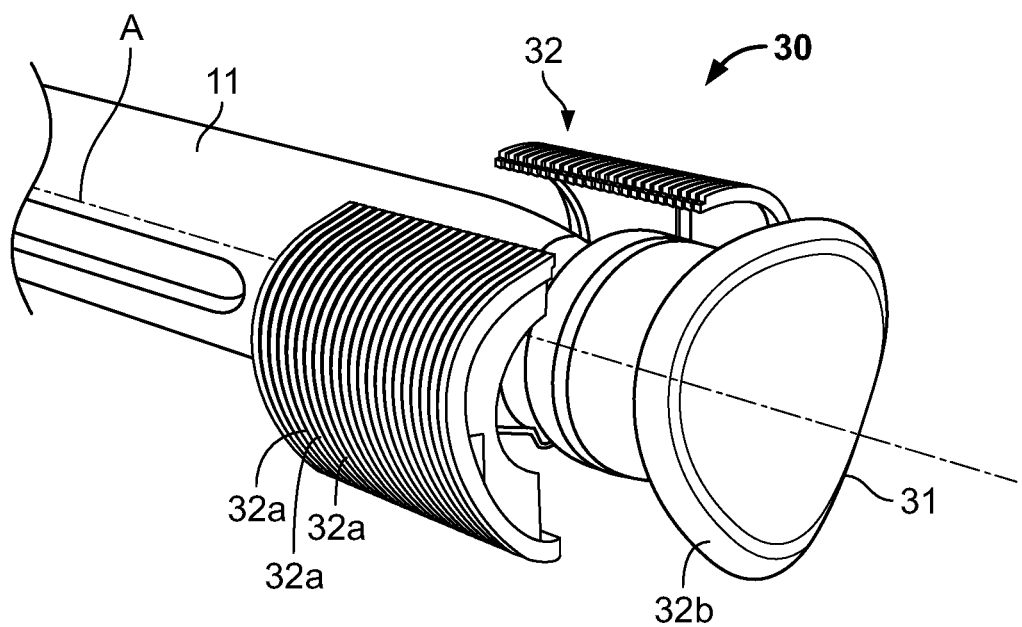
FIG. 3 comprises an assembly view of a portion of the drug delivery assembly of FIG. 2 in accordance with various embodiments of the invention.

The tubular member 32 may be disposed about (e.g., surround) the distal end of the housing 11 and/or a distal end of a delivery cannula (not illustrated), and may removably attach the signal cap 30 to the housing 11. As shown in FIG. 3, the tubular member 32 may be assembled by fitting two interlocking and generally C-shaped members over the distal end of the housing 11. In some embodiments, the signal cap 30 may form an interference or snap fit with the distal end of the housing 11. A frictional force associated with the interference or snap fit may be overcome by manually pulling the signal cap 30 in a distal direction away from a housing 11. The interference or snap fit may be formed by configuring an inner diameter of the tubular member 32 to be slightly smaller than an outer diameter of a distal end of the housing 11. Alternatively, or additionally, the tubular member 32 may have a tearable or weakened member (not illustrated) that connects the tubular member 32 to the distal end of the housing 11 and which can be broken or torn by the patient when pulling the signal cap 30 away from the housing 11. The tubular member 32 may further include a plurality of outwardly protruding ribs 32a designed to help a patient grip the tubular member 32 to detach it from the housing 11. The ribs 32a may be useful to elderly and disabled patients who have below average gripping strength.

The cover member 31 may be fixed to a distal end of the tubular member 32 and may completely cover an opening formed at the distal end of the tubular member 32. A distal end surface of the cover member 31 may be planar such that the drug delivery device 10 can be disposed on planar surface in an upright configuration without falling over. Also, an outer peripheral portion of the cover member 31 may be wider than an outer peripheral portion of the tubular member 32 such that a ledge or overhang 32b is formed at the interface between the cover member 31 and the tubular member 32. This ledge 32b may help prevent a patient's fingers from slipping over the cover member 31 when trying to pull the signal cap 30 off of the housing 11.

Since the housing 11 may have a circular cross section resulting in a round exterior side surface, the drug delivery device 10 may be susceptible to unintentionally rolling across a surface when it is placed on its side. To inhibit or prevent the drug delivery device 10 from rolling across a surface when placed on its side, the tubular member 32 and/or the cover member 31 may be formed with at least one roll inhibiting exterior side surface. The at least one roll inhibiting exterior side surface may extend between proximal and distal ends of the tubular member 32 and/or between proximal and distal ends of the cover member 31. The at least one roll inhibiting exterior side surface of the tubular member 32 and/or the cover member 31 may be parallel to a longitudinal axis A of the drug delivery device 10 and/or perpendicular to the distal end surface of the cover member 31.

Figure 2:
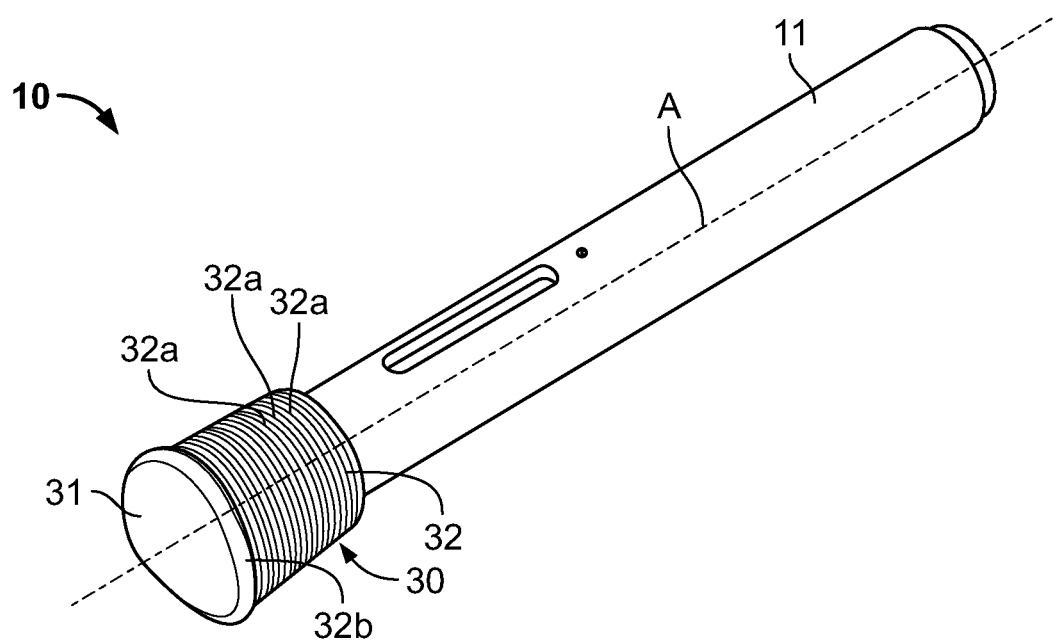
FIG. 2 comprises a perspective view of a drug delivery system in accordance with various embodiments of the invention.
Figure 4:
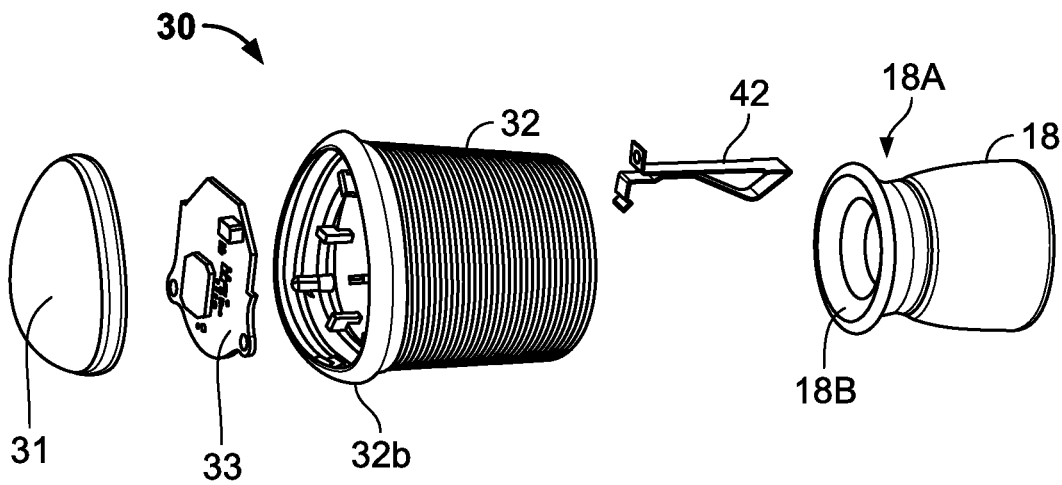
FIG. 4 comprises an exploded view of a cap assembly for an autoinjector in accordance with various embodiments of the invention.

In the embodiment illustrated in FIGS. 2-4, the tubular member 32 has a triangular cross section formed by three planar exterior side surfaces, and the cover member 31 has a triangular cross section forming three planar exterior side surfaces. The cross section described herein is the one which is perpendicular to the longitudinal axis A of the drug delivery device 10. Each of the planar exterior side surfaces is an example of a roll inhibiting exterior side surface. This is because each of the planar exterior side surfaces is configured to inhibit (e.g., prevent) the signal cap 30 and/or the drug delivery device 10 from rolling across a support surface when the respective planar exterior side surface rests against the support surface.

As used herein, the term "planar" is hereby defined to mean flat or substantially flat. As shown in FIGS. 2-5, each of the planar exterior side surfaces balloons outwardly and thus has a slight curvature. While the planar exterior side surfaces are not exactly flat, they are nonetheless substantially flat and therefore are considered to be "planar" in accordance with principles of the present disclosure. In alternative embodiments, one or more of the planar exterior side surfaces may be perfectly flat such that it does not have any curvature. Regardless of whether the planar exterior side surfaces have a flat configuration or a substantially flat configuration, the planar exterior side surfaces may have the ability to inhibit (e.g., prevent) rolling of the signal cap 30 and/or the drug delivery device 10.

The anti-roll functionality of the signal cap 30 may be achieved through a variety of different shapes and sizes of the tubular member 32 and/or the cover member 31. In some embodiments, only the tubular member 32, or only the cover member 31, may have a triangular cross section. Other cross-sectional shapes of the tubular member 32 and/or the cover member 31 are capable of preventing or inhibiting rolling including, but are not limited to, a hemisphere, a square, a rectangle, a pentagon, hexagon, or any other polygonal shape. Also, the vertices or corners formed by the one or more planar exterior side surfaces of the tubular member 32 and/or the cover member 31 may be rounded so that the vertices or corners are not likely to cause injury or pain to a patient while gripping the signal cap 30. It should be noted that the particular shape of the signal cap 30 illustrated in FIGS. 2-4 is an aesthetic feature not dictated by function.

In an alternative embodiment, the drug delivery device 10 may include a second removable sterile barrier (not shown), separate from the signal cap 30, which attaches directly to the reservoir and surrounds the delivery cannula. In such an embodiment, the signal cap 30 may cover and/or surround the second removable sterile barrier.

The signal cap 30 can be designed for single, one-time use, or for multiple uses. The embodiment of the signal cap 30 may be assembled by fitting each of the C-shaped members separately around the distal end of the housing 11 and then fixing the C-shaped members together with an adhesive. In an alternative embodiment (not illustrated), the C-shaped members may be hinged together in a clam shell arrangement. In such an alternative embodiment, after removing the signal cap 30 from the housing 11, it may be possible to re-attach the signal cap 30 to the housing 11 (or the housing of another drug delivery device) by opening the C-shaped members like a clam shell and then fitting them around the distal end of the housing 11. The non-hinged ends of the C-shaped members may include a locking mechanism (e.g., mating locking tabs and/or slots) so that the C-shaped members can be secured to each other after they are secured around the housing 11. Substantial cost savings may be realized by the re-usable configuration of the signal cap 30 since the electronic component or components 33 onboard the signal cap 30 can be used more than once. In still further embodiments, the signal cap 30 may be manufactured in one piece, and then installed axially onto the housing 11 of the drug delivery device 10.

Figure 6A:
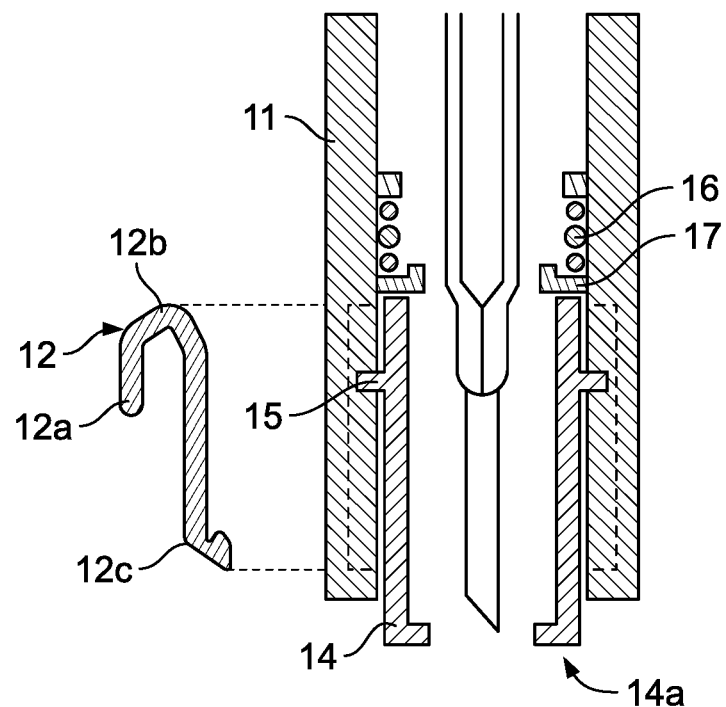
FIG. 6A comprises a cross-sectional view of a drug delivery device assembly having a movable needle guard in accordance with various embodiments of the invention.
Figure 6B:
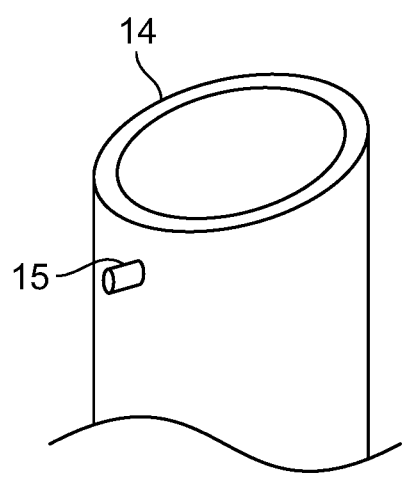
FIG. 6B comprises a perspective view of the needle guard of FIG. 6A in accordance with various embodiments of the invention.
Figure 7:
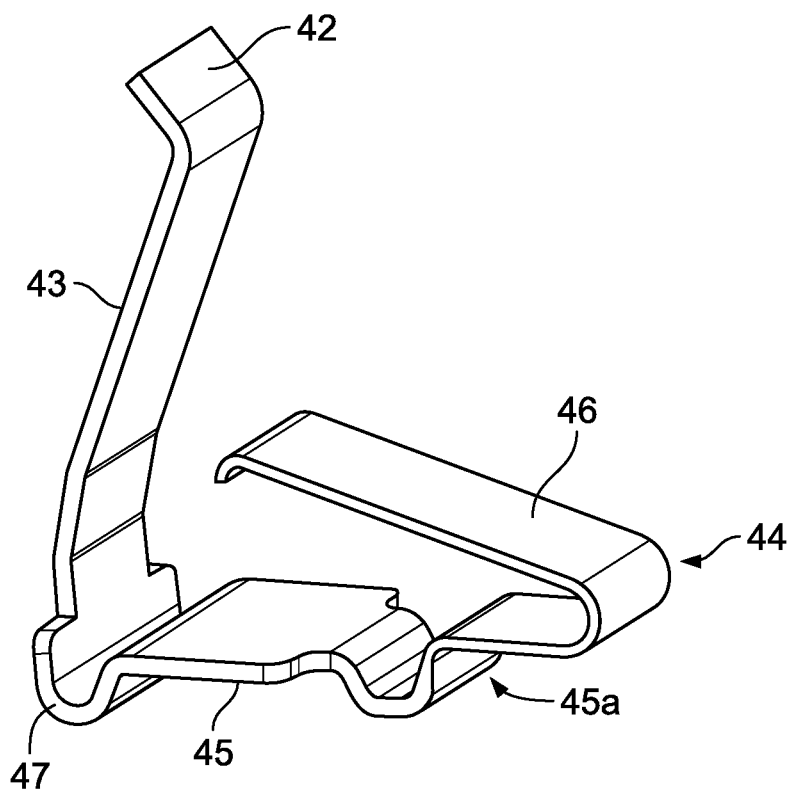
FIG. 7 comprises a perspective view of a first embodiment of a spring lever being rotatable between a first and a second configuration in accordance with various embodiments of the invention.

As illustrated in FIGS. 6A and 6B, the drug delivery assembly 10 includes a guard 14 which engages an inner surface of the housing 11 and is movable between at least a first, second, and third position relative to the housing 11. The guard 14 is adapted to at least partially restrict external contact with the cannula. In one example, the guard 14 includes a protrusion 15 extending from an outer surface which engages a groove 12 disposed on an inner surface of the housing 11. This groove 12 may include a first section defining a first stop 12a, a second section defining a second stop 12b, and a third section defining a third stop 12c which maintain the protrusion 15 (and thus, the guard 14) at first, second, and third positions. The first section may include a substantially axial portion proximal to the first stop 12a and an angled portion proximal to the second stop 12b. The second section extends in a substantially axial direction between the second stop 12b and the third stop 12c. The third section may also include an angled portion and a substantial axial portion. A spring 17 may be disposed within the housing 11 which contacts a ledge 17 to assert a force against the guard 14.

As previously stated, the guard 14 may be slidably moved to a first, second, and third position relative to the housing 11. When the guard 14 is in the first position, a proximal end 14a thereof extends a length slightly further than the tip of the cannula. Additionally, in this first position, the protrusion 15 is located in the first stop 12a, and thus the spring 16 is restricted from displacing the guard 14 further in the axial direction.

When the user wishes to administer the drug in the drug delivery device 10 (assuming the device 10 is in the required state for administering the drug), they may press the proximal end 14a of the guard 14 against their skin and continue to press until the spring 16 begins to compress, thereby moving the guard 14 into the housing 11 and exposing the cannula such that it penetrates the surface of the skin. During this time, the protrusion 15 traverses the groove and contacts the second stop 12b which limits movement of the guard 14 and restricts the cannula from being further inserted into the user. When the protrusion 15 contacts the second stop 12b of the groove 12, the guard 14 is in the second position.

Upon completion of the drug being administered, the user removes the cannula from their body and the spring 16 expands. The protrusion 15 then traverses the second and third sections of the groove 12 and ultimately contacts the third stop 12c. As a result, the protrusion 15 is maintained in the second catch whereby lateral movement of the guard 14 is restricted. As a result, the guard 14 is maintained in an "extended" third position in which the cannula is not exposed and rather is in a recessed state relative to the guard 14.

It is understood that in some examples, the groove may be disposed on a surface of the guard 14, and the housing 11 may include the protrusion 14. In such a configuration, the slidable movement between the housing 11 and the guard 14 is maintained. Further, it is understood that there may be any number of grooves and corresponding protrusions disposed on the housing 11 and the guard 14. By using additional grooves and protrusions, additional stability during sliding movement may be achieved.

Figure 23:
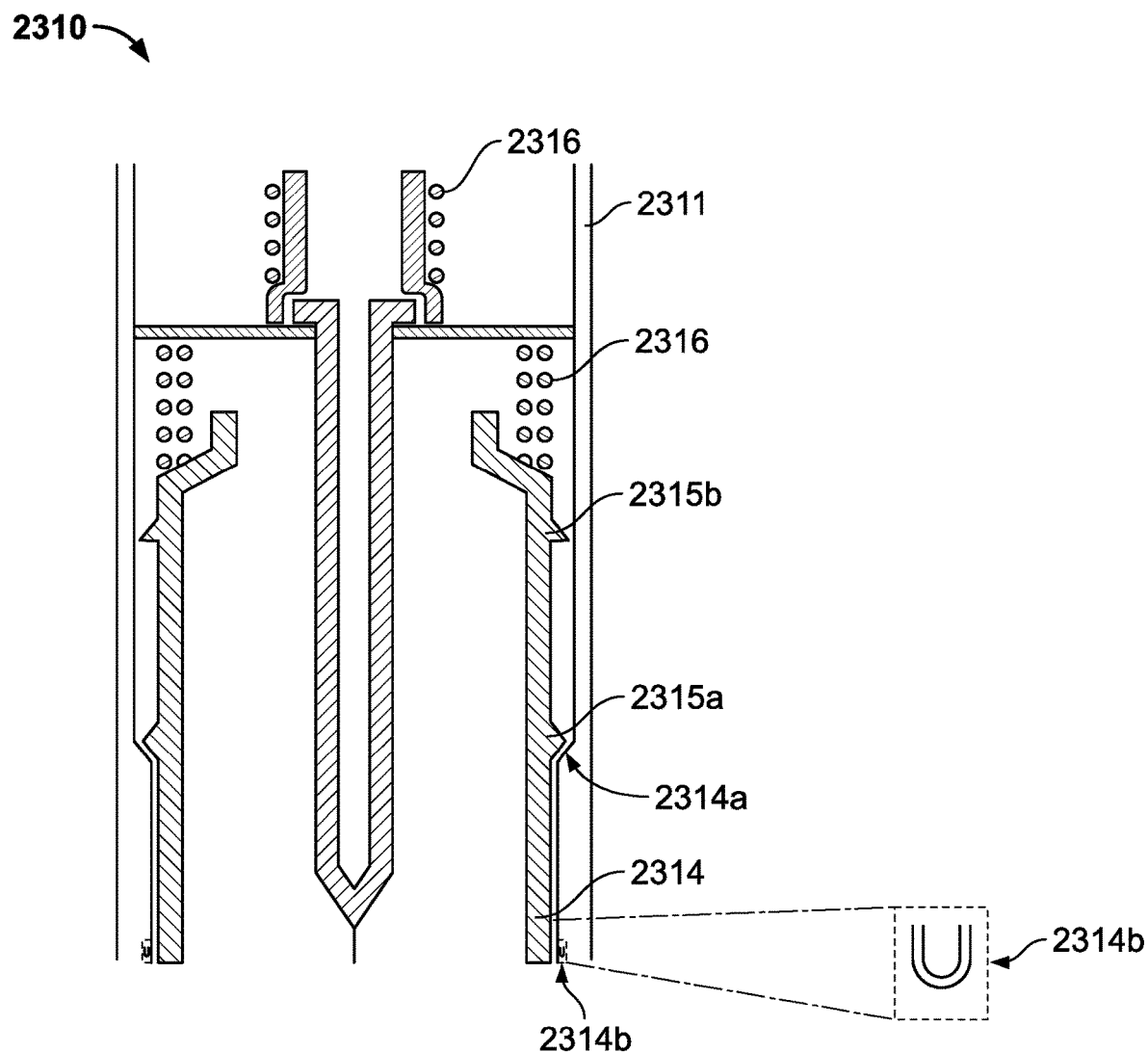
FIG. 23 comprises a cross-sectional view of an alternate drug delivery device having a movable needle guard in accordance with various embodiments of the invention.

Further, as illustrated in FIG. 23, in some examples, the guard 2314 may include a number of protrusions 2315a, 2315b located at different positions along a longitudinal length thereof. These protrusions 2315a, 2315b may engage a bevelled 2314a region of the guard 2314 which contacts the protrusions to limit movement of the guard 2314 relative to the housing 2311. Any number of safety springs 2316 may be used to bias the guard 2314 towards an extended position.

In a first position, the first protrusion 2315a is disposed adjacent to the bevelled area 2314a and thus causes the guard 2314 to rest in such a configuration due to a frictional interaction therebetween. The spring force exerted by the safety spring 2316 is insufficient to urge the first protrusion 2315a past the bevelled area 2314a when the guard 2314 is in a resting position. Upon administering the drug, the safety spring 2316 or springs compress until the device 2310 is removed from the user. The spring force generated by the compression is sufficient to urge the guard 2314 to extend relative to the housing 2311. The first protrusion 2315a then advances past the bevelled region 2314a, and the second protrusion 2315b is adapted to frictionally engage or catch the bevelled region 2314a. As a result, the guard 2314 is positioned in an extended configuration where the cannula is not exposed. The housing 2311 may also include a material relief portion 2314b comprising a cut-out portion of the housing 2133 which ensures the first protrusion 2315a may move past an end of the housing 2311. It is understood that the device 2310 may have any number of these components positioned around the perimeter of the housing 2311. Other examples are possible.

Turning to FIGS. 7-12b, an exemplary cap assembly is herein described. It is understood that the cap assembly may be used with any of the exemplary assemblies and components described herein. Generally speaking, the switch assembly 40 is adapted to cause the power source 35 to provide power to the electronic component 33 when the signal cap 30 is removed from the housing 11, restrict the power source 35 from providing power to the electronic component 33 when the signal cap 30 is coupled to the housing 11 and the guard 14 is in the first position, and cause the power source 35 to provide power to the electronic component 33 when the signal cap 30 is coupled to the housing 11 and the guard 14 is in the third position.

The switch assembly 40 may include the switch 41 disposed in the signal cap 30 and being coupled to the electronic component 33. The switch 41 is movable between an activated position and a deactivated position, and causes the power source 35 to provide power to the electronic component 33 when in the activated position. The switch 41 may be constructed of or include a resilient material which causes the switch 41 to be urged in either the deactivated or the activated position as desired. It is understood that the switch 41 may be positioned in any number of locations relative to the electronic component 33 such as, for example, on an upper surface of the electronic component 35 as illustrated by FIG. 5A or on a lower surface of the electronic component 35 as illustrated in FIG. 5B. The switch assembly 40 further includes a spring lever 42. At least a portion of the spring lever 42 is movable between at least a first position and a second position.

When the signal cap 30 is coupled to the housing 11 and the guard 14 resides in the first position, a portion of the housing 11 contacts the spring lever 42 and moves or urges the spring lever 42 into the first position. In this first position, the spring lever urges the switch into the deactivated position. When the signal cap 30 is coupled to the housing 11 and the guard 14 occupies the third position, the spring lever 42 resides outside of the first position such that the switch 41 occupies the activated position. When the signal cap 30 and the components disposed therein are removed from the housing 11, the spring lever 41 remains out of contact with the drug delivery device 10 and occupies the second position such that the switch 41 occupies the activated position. It is understood that when the signal cap 30 is coupled to the housing and the guard occupies the third position, the spring lever may also occupy the second position such that the switch 41 occupies the activated position.

The spring lever 42 illustrated in FIGS. 7-12B is rotatable and includes a first section 43 and a second section 44 extending from the first section 43. The second section 44 has a first length 45 having a switch engagement region 45a and a second length 46 forming a substantially U-shaped section with the first length 45. In other words, the second length 46 of the second section 44 turns back on the first length 45 and extends towards the first section 43. It is understood that the first and the second lengths 45, 46 may form any number of shapes or configurations. The spring lever 42 includes a rotatable coupling 47 which engages a portion of the cap assembly 30 to rotate between the first and the second configurations. The spring lever 42 may be a solid, unitary member or may include a number of sections coupled to each other using any number of generally known approaches. The spring lever 42 may include a resilient portion and may also include a rigid portion.

The spring lever 42 is disposed in the signal cap 30 whereby the rotatable coupling 47 engages an extension 36 of the signal cap which maintains the spring lever 42 in the signal cap 30 while permitting rotation between a first and a second configuration. When the spring lever 42 is rotated to the first configuration, the switch engagement region 45 does not contact the switch 41 which is thereby positioned in a deactivated position and thus the electronic component 33 remains unpowered. When the spring lever 42 is rotated to the second configuration, the switch engagement region 45 contacts the switch 41 which is thereby positioned in the activated position and thus the electronic component 33 is powered.

Figure 8:
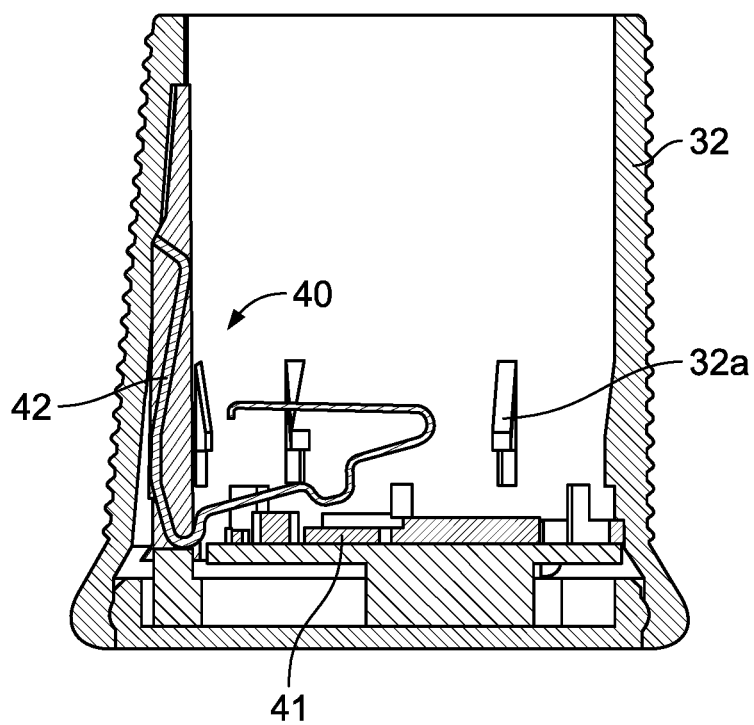
FIG. 8 comprises a cross-sectional view of a cap assembly having the spring lever of FIG. 7 disposed therein in accordance with various embodiments of the invention.
Figure 9A:
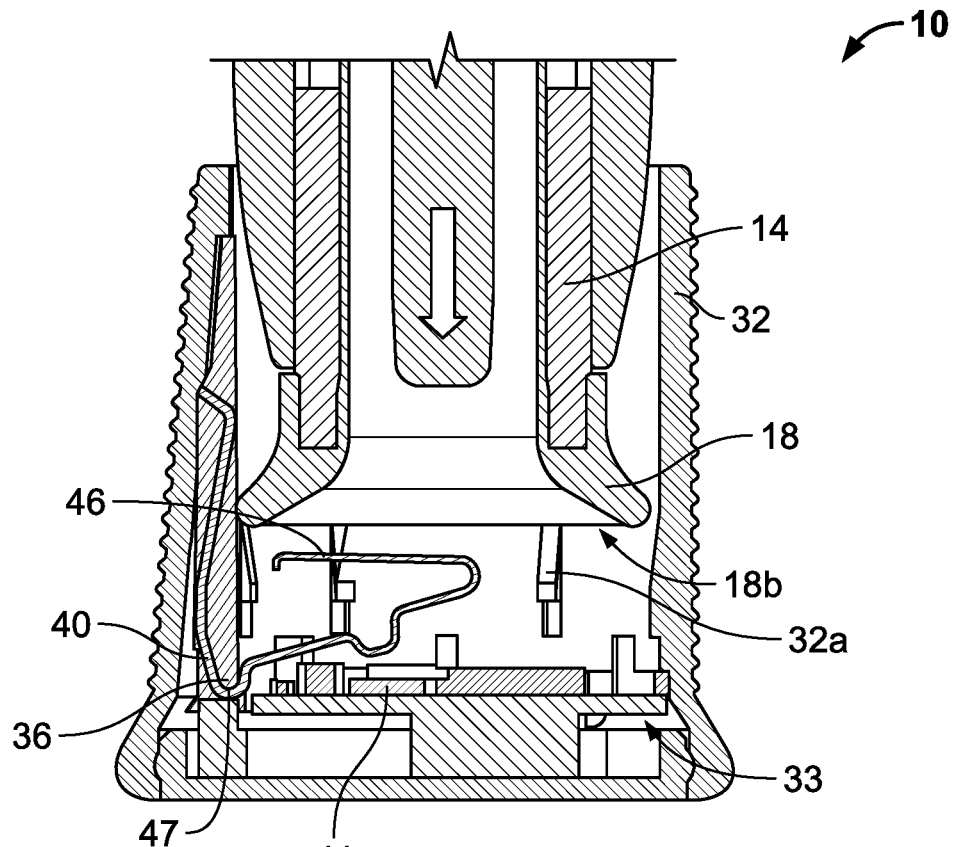
FIGS. 9A and 9B comprise cross-sectional views of the cap assembly of FIG. 8 having a needle shield remover being inserted into the cap assembly in FIG. 9A and being fully disposed in the cap assembly in FIG. 9B in accordance with various embodiments of the invention.
Figure 9B:
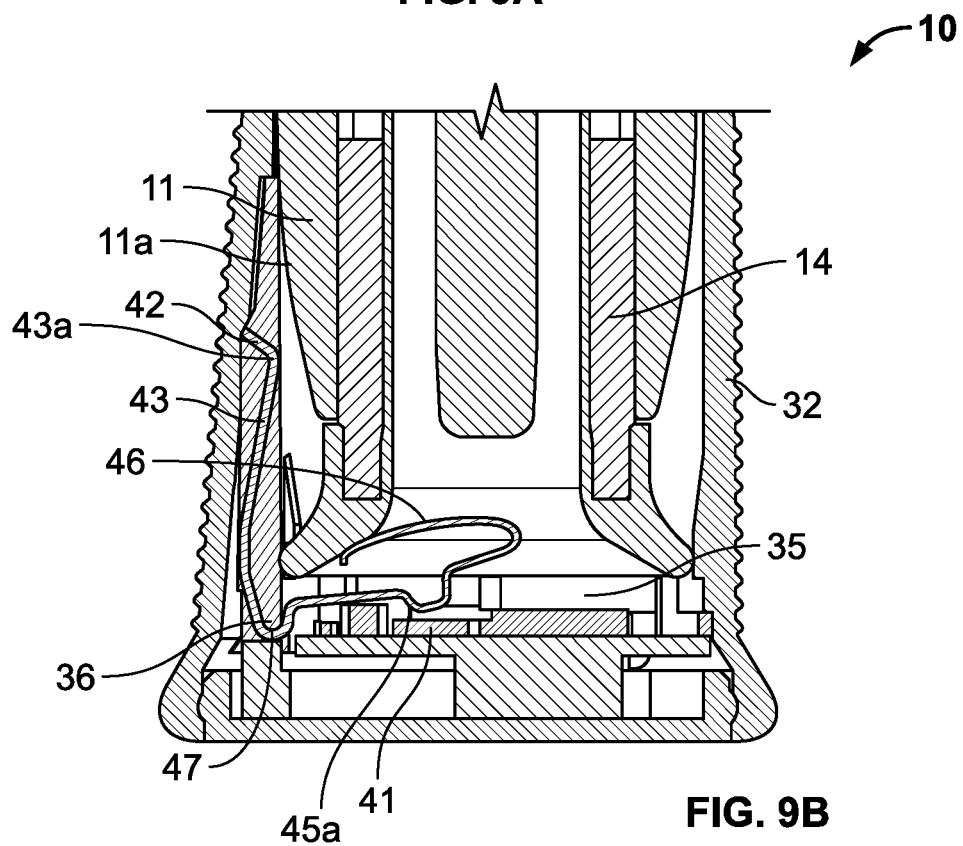

Turning to FIGS. 8, 9A, and 9B, the coupling of the device 10 to the signal cap 30 is described. The signal cap 30 includes any number of protrusions 32a designed to engage a needle shield remover 18, which secures the device 10 to the signal cap 30. An outer ledge or flange 18a of the needle shield remover 18 is adapted to engage the region under the tab 32a so that when signal cap 30 is removed from the housing 11, the needle shield remover 18 remains disposed in the signal cap 30 while the remainder of the device 10 is removed therefrom. When the device 10 is initially coupled to the signal cap 30, a lower surface 18b of the needle shield remover 18 contacts the second length 46 of the spring lever 42 to exert a force which biases the spring lever 42 in the second configuration.

As illustrated in FIG. 9B, an outer surface 11a of the housing 11 comes into contact with a bend 43a in the first section 43 and exerts a force on the first section 43. This force exerted by the housing 11 is greater than the force exerted by the needle shield remover 18, and thus the spring lever 42 is forced to rotate into the first configuration in which the switch engagement region 45a does not engage the switch 41, thereby positioning the switch 41 in the deactivated position. As previously stated, this configuration causes the electronic component 33 to be in an unpowered state.

Figure 10:
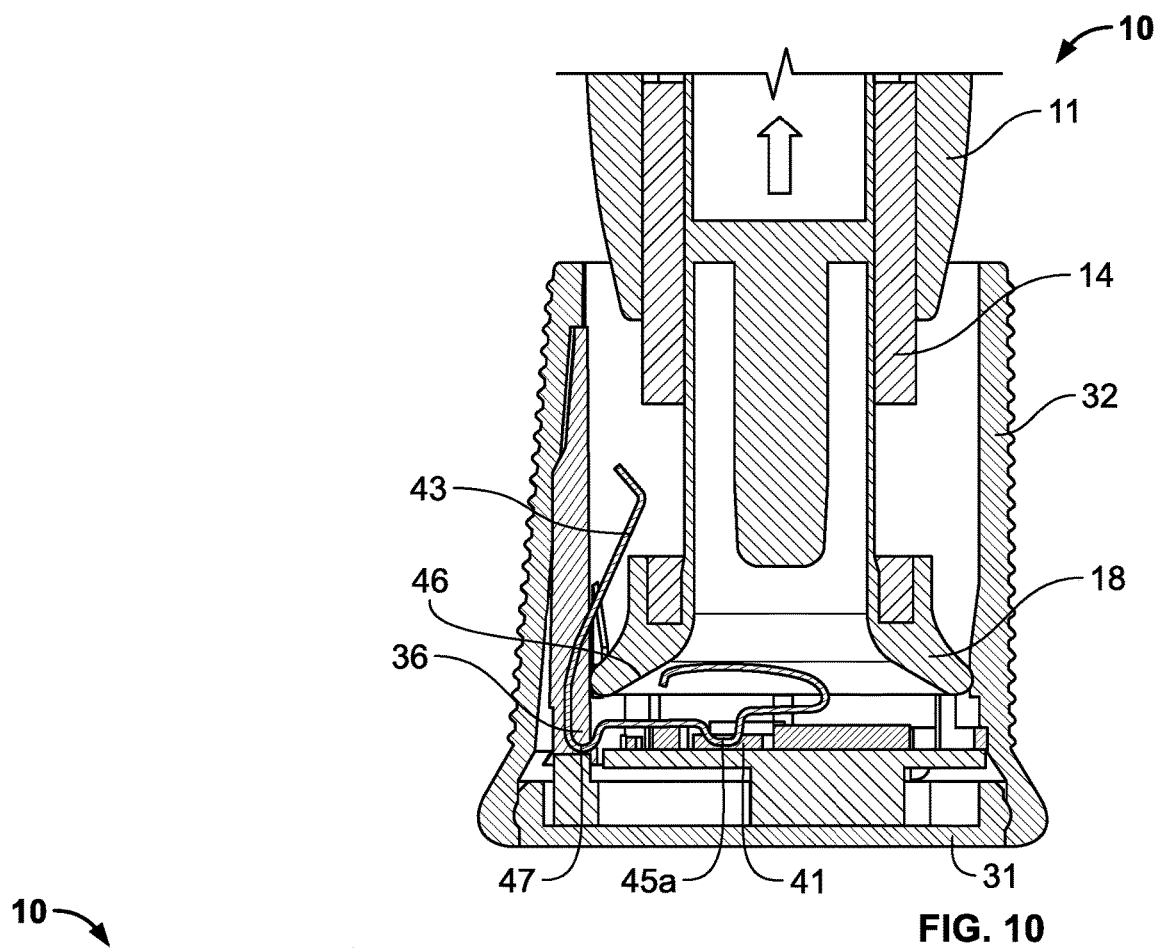
FIG. 10 comprises a cross-sectional view of the cap assembly of FIGS. 8-9 having the cap being removed for the purpose of administering a medication in accordance with various embodiments of the invention.

As illustrated in FIG. 10, the signal cap 30 is in the process of being removed from the device 10 for the purposes of administering the drug. During this process, the first section 43 of the spring lever 42 does not contact the housing 11 or any other portion of the device, and thus the force exerted by the needle shield remover 18 causes the second length 46 of the spring lever 42 to rotate about the extension 36 to the second configuration whereby the switch engagement region 45a engages the switch 41, thereby positioning the switch 41 in the activated configuration which causes the power source 35 to power the electronic component 33.

Figure 11A:
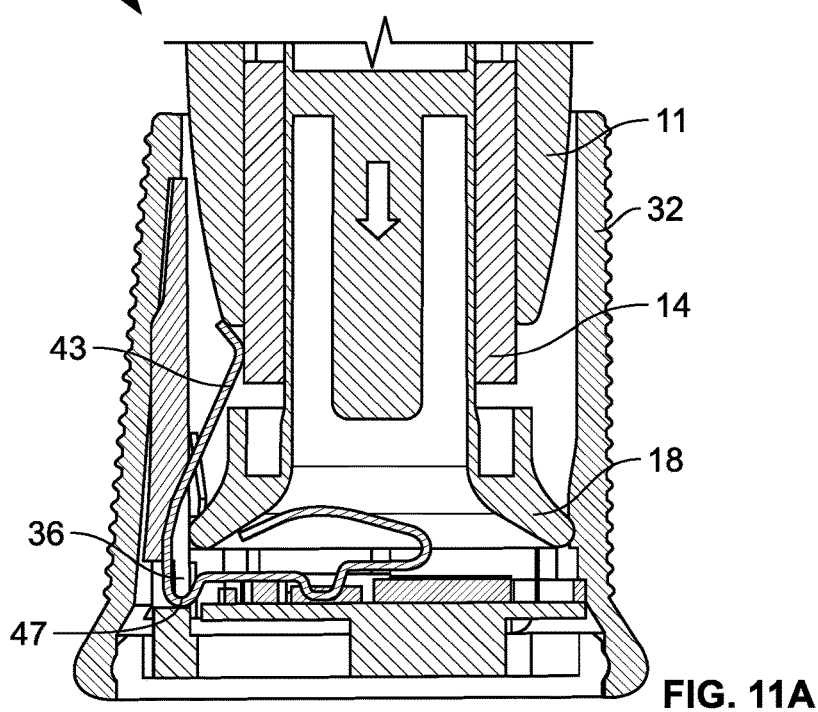
FIGS. 11A and 11B comprise cross-sectional views of the cap assembly of FIGS. 8-10 during recapping of the cap assembly to the drug delivery device prior to administering the medication in accordance with various embodiments of the invention.
Figure 11B:
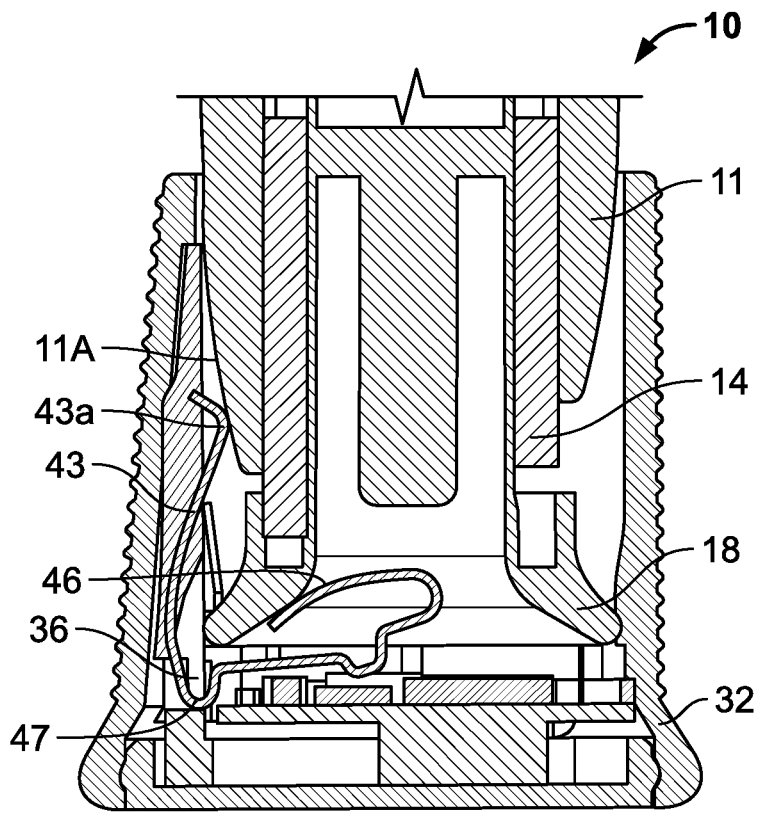

As illustrated in FIGS. 11A and 11B, if the user decides they do not wish to administer the drug at the present time, the signal cap 30 may be recapped onto the device 10. When this occurs, the outer surface 11a of the housing 11 again contacts the bend 43a of the spring lever 42 and thereby exerts a force on the spring lever 42 which causes the spring lever 42 to rotate about the extension 36 until positioned in the first configuration, thereby positioning the switch 41 in the deactivated position. As previously stated, this configuration causes the electronic component 33 to be in an unpowered state. As a result, the power source 35 is not drained and will be ready to provide power to the electronic component 33 as needed.

Figure 12A:
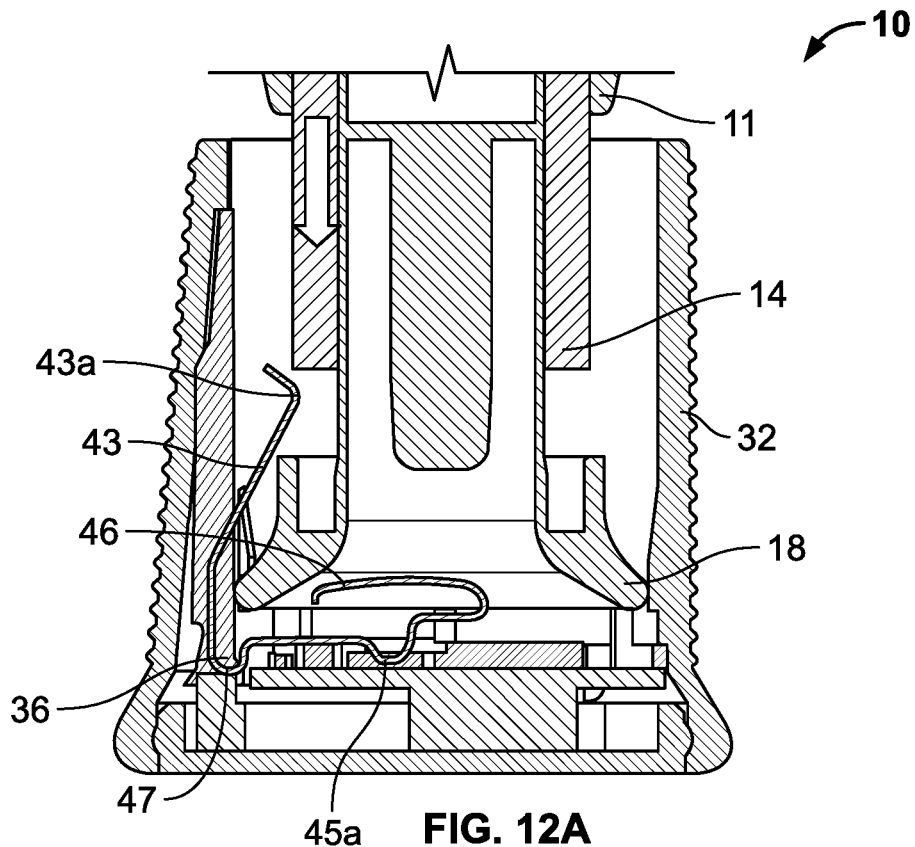
FIGS. 12A and 12B comprise cross-sectional views of the cap assembly of FIGS. 8-11 after recapping of the cap assembly to the drug delivery device after administering the medication in accordance with various embodiments of the invention.
Figure 12B:
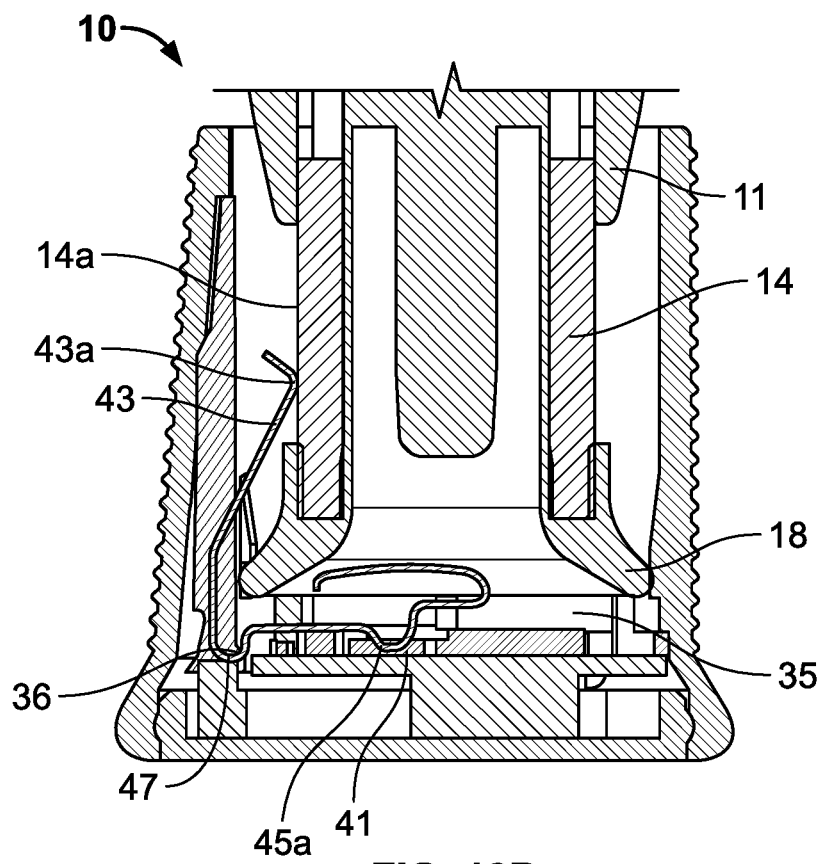
Figure 13:
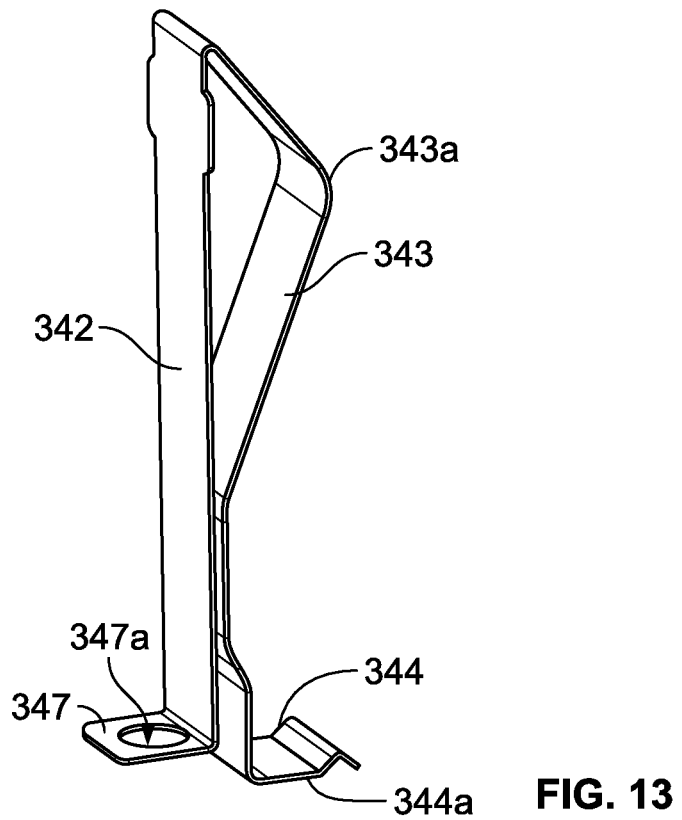
FIG. 13 comprises a perspective view of a second embodiment of a spring lever being toggled between a first and a second configuration in accordance with various embodiments of the invention.

As illustrated in FIGS. 12A and 12B, the user has again removed the signal cap 30 and administered the drug contained in the device 10. As previously described, the guard 14 is now disposed in the third position. Because of the extension of the guard 14, the outer surface 11a of the housing 11 is precluded from contacting the spring lever 42 in a manner which generates a sufficient force to urge the spring lever 42 into the first configuration. In one embodiment, an outer surface of the guard 14a may come in contact with the bend 43a of the spring lever 42. Alternatively, the guard 14 may not contact the spring lever 42 at all. Regardless as to whether the spring lever 42 contacts the guard 14 or is located in a void region, the force exerted by the needle shield remover 18 is large enough to overcome any forces on the first section 43 and thus urges the spring lever 42 into the second configuration whereby the switch engagement region 45a engages the switch 41, thereby positioning the switch 41 in the activated configuration which causes the power source 35 to power the electronic component 33. As a result, the electronic component 33 may continue operating to sense, store, and/or transmit data as desired.

It is understood that in some embodiments, the first section 43 of the spring lever 42 may not include a bend, but rather may include a generally inwardly tapered region which contacts a portion of the housing 11. Further, the housing 11 may have a generally tapered end which creates a smooth coupling process between the device 10 and the signal cap 30. Other examples and/or configurations are possible.

Turning to FIGS. 13-17, an alternative signal cap assembly 300 is provided. It is understood that features and/or elements which are similar to those previously described will contain similar two-digit suffixes as those previously provided and, due to similarities in function, will not be fully described for the sake of brevity. For example, the signal cap assembly includes a signal cap 330 which bears similarities to the signal cap 30 previously described. The signal cap assembly 300 includes a signal cap 330 defining a cap body and an opening, an electronic component 333 at least partially disposed in the signal cap 330, a power source 335 at least partially disposed in the signal cap 330, a switch 341 at least partially disposed in the signal cap 330, and a spring lever 342 at least partially disposed in the signal cap 330. The switch 341 is movable between an activated position and a deactivated position and causes the power source to provide power to the electronic component 333 when in the activated position. The spring lever 342 includes a first portion 343 forming a bend 343a extending radially away from the cap body and a second portion 344 having a switch engagement region 344a.

In one example, the spring lever 342 is coupled to the signal cap 30 by disposing a coupling region 347 between the cover member 331 and the tubular member 332. Either one of the cover member 331 or the tubular member 332 may include a protrusion which engages a hole 347a formed in the coupling region 347. It is understood that any number of coupling devices and/or components may be used to secure the spring lever 342.

In this configuration, the spring lever 342 is biased in a manner in which causes the first portion 343 to extend inwardly. As a result, the needle shield guard 318 does not create a force which urges the spring lever 342 into a configuration.

Figure 14:
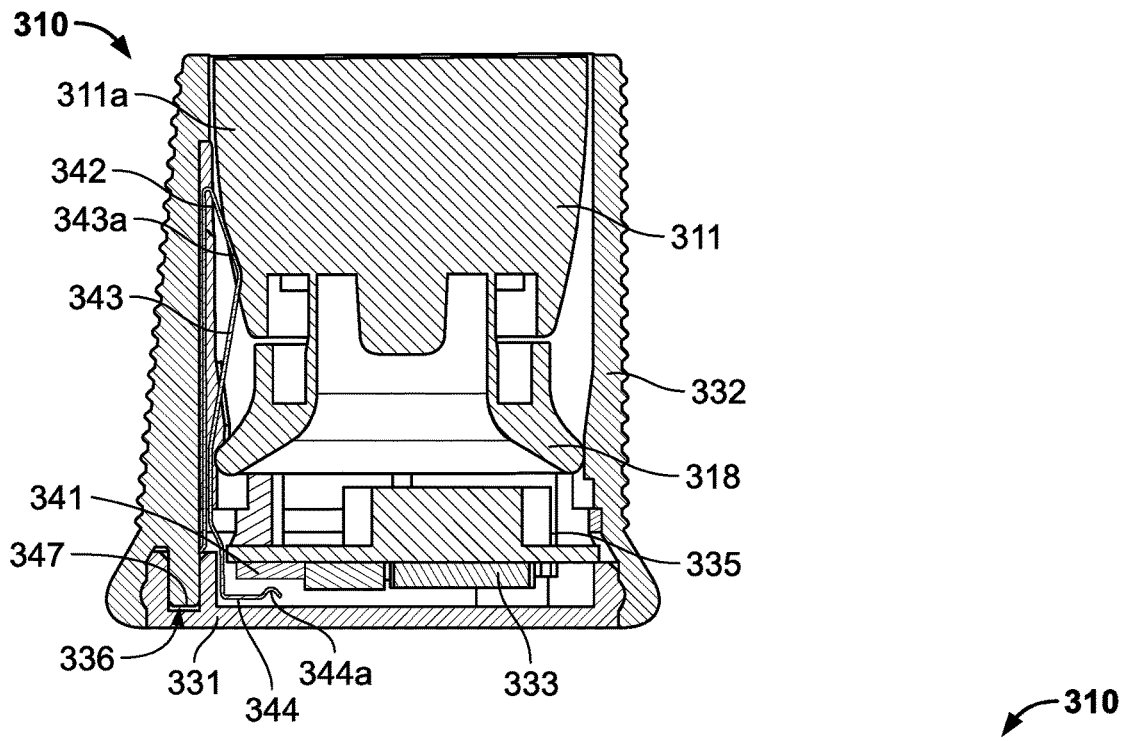
FIG. 14 comprises a cross-sectional view of a cap assembly having the spring lever of FIG. 13 disposed therein in accordance with various embodiments of the invention.

As illustrated in FIG. 14, when the device 310 is coupled to the signal cap 330, the first portion 343 of the spring lever 342 contacts an outer surface 311a of the housing 311, thereby generating a first force which urges the first portion 343 of the spring lever 342 towards the tubular member 332. This force may be a radial force exerted towards the cap wall, thereby compressing the first portion 343 and causes the bend 343a to extend, which in turn causes the switch engagement region 344a of the second portion 344 to disengage the switch 341. Upon disengaging the switch 341, the switch is positioned in the deactivated position. This configuration causes the electronic component 333 to be in an unpowered state.

Figure 15:
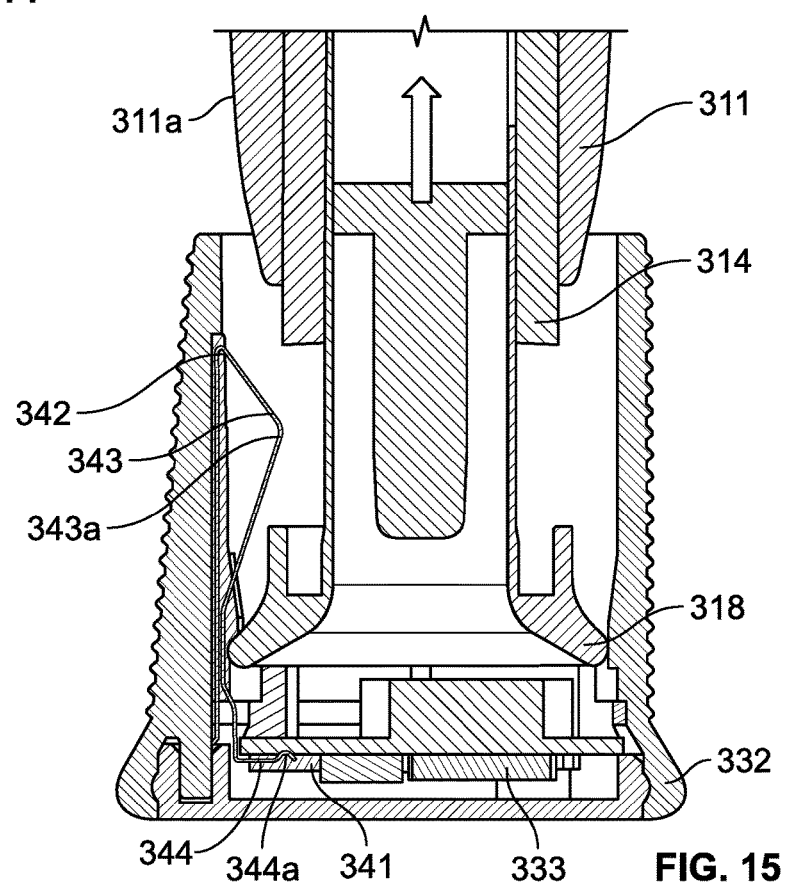
FIG. 15 comprises a cross-sectional view of the cap assembly of FIGS. 13 and 14 having the cap being removed for the purpose of administering a medication in accordance with various embodiments of the invention.

As illustrated in FIG. 15, the signal cap 330 is in the process of being removed from the device 310 for the purposes of administering the drug. During this process, the first portion 343 of the spring lever 342 does not contact the housing 311 or any other portion of the device, and thus the first portion 343 is in a bent configuration. This bent configuration causes the switch engagement region 344a to engage the switch 341, thereby positioning the switch 341 in the activated configuration which causes the power source 335 to power the electronic component 333.

Figure 16A:
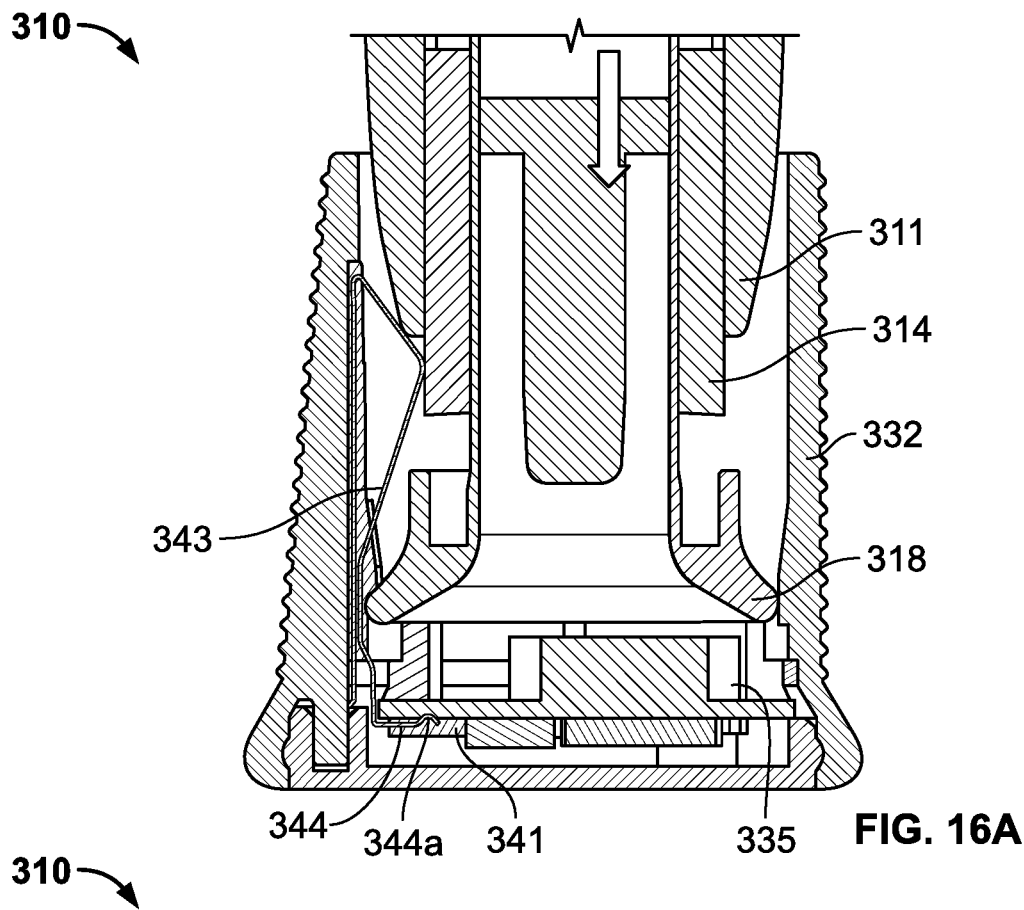
FIGS. 16A and 16B comprise cross-sectional views of the cap assembly of FIGS. 13-15 during recapping of the cap assembly to the drug delivery device prior to administering the medication in accordance with various embodiments of the invention.
Figure 16B:
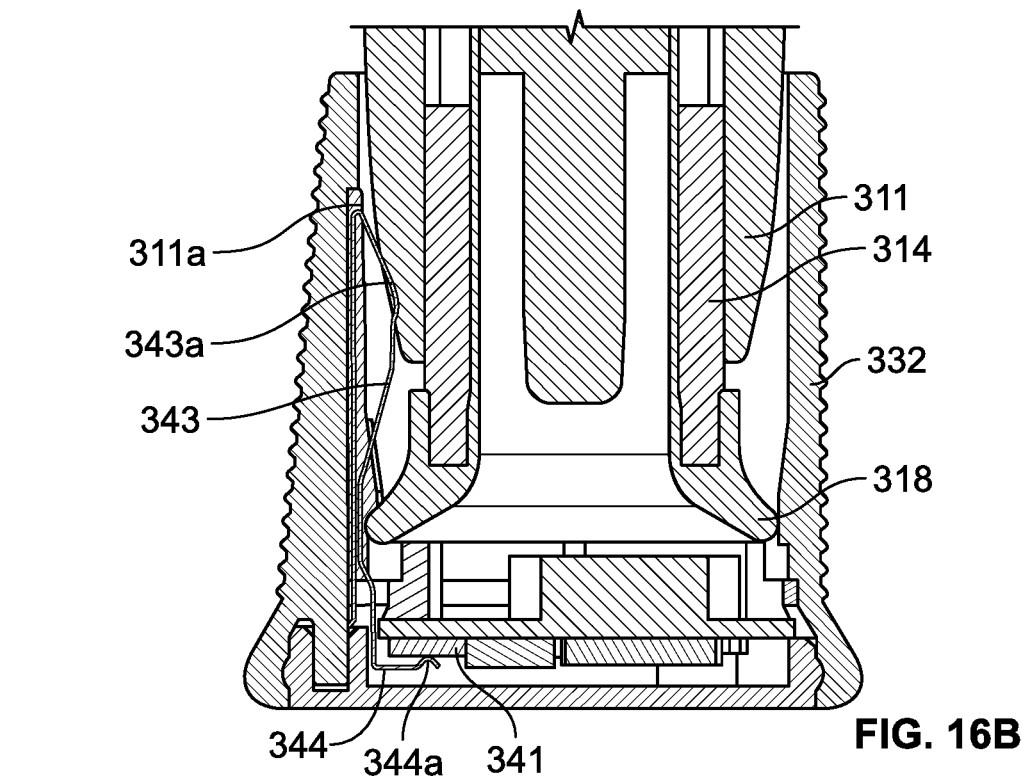
Figure 17:
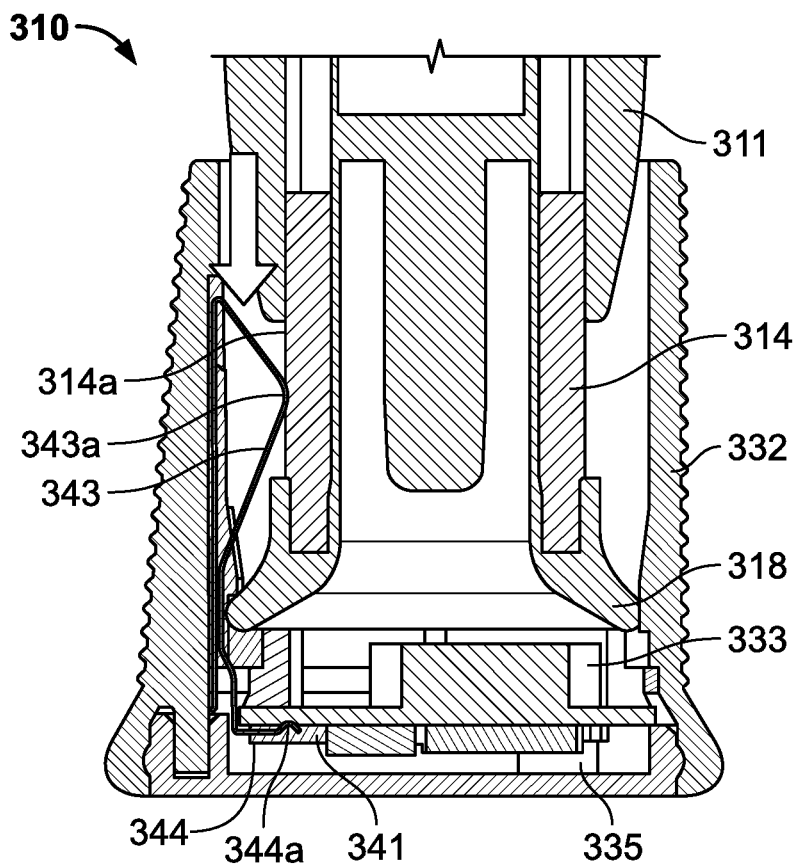
FIG. 17 comprises a cross-sectional view of the cap assembly of FIGS. 13-16 after recapping of the cap assembly to the drug delivery device after administering the medication in accordance with various embodiments of the invention.
Figure 18:
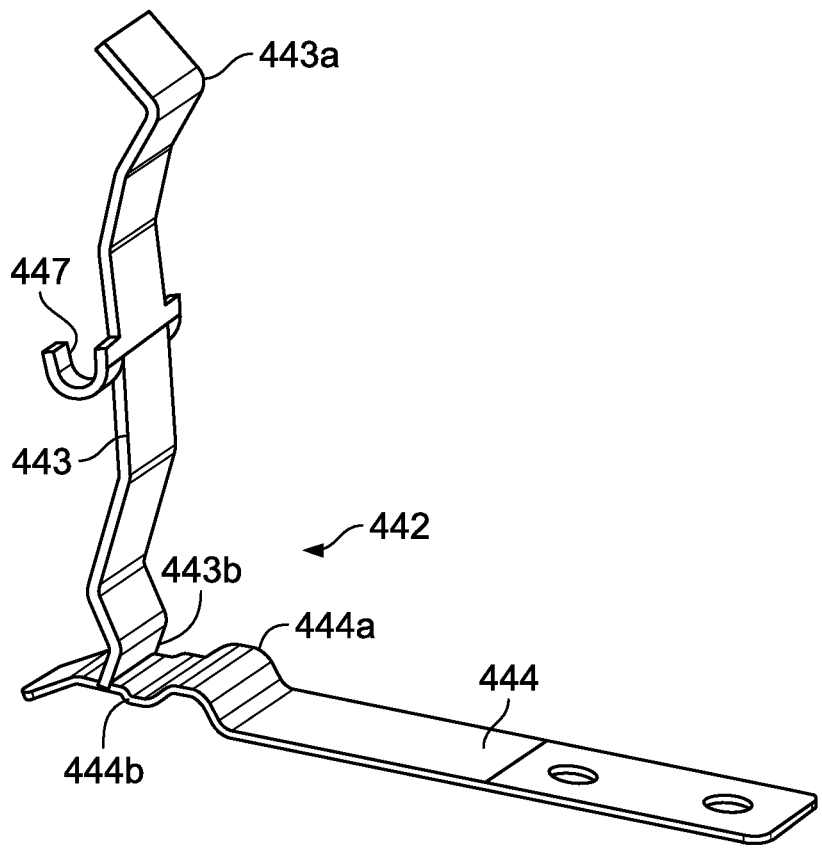
FIG. 18 comprises a perspective view of a third embodiment of a spring lever being toggled between a first and a second configuration in accordance with various embodiments of the invention.

As illustrated in FIGS. 16A and 16B, if the user decides they do not wish to administer the drug at the present time, the signal cap 330 may be rec3apped onto the device 310. When this occurs, the outer surface 311a of the housing 311 again contacts the bend 343a of the spring lever 342 and thereby exerts a force on the spring lever 342 which causes the spring lever 342 to extend, which in turn causes the switch engagement region 344a of the second portion 344 to disengage the switch 341, thereby positioning the switch 341 in the deactivated position. As previously stated, this configuration causes the electronic component 333 to be in an unpowered state. As a result, the power source 335 is not drained and will be ready to provide power to the electronic component 333 as needed.

As illustrated in FIG. 17, the user has again removed the signal cap 330, administered the drug contained in the device 310, and returned the signal cap 330 to the device 310. As previously described, the guard 314 is now disposed in the third position. Because of the extension of the guard 314 relative to the housing 311, the outer surface 311a of the housing 311 is precluded from contacting the spring lever 342 in a manner which generates a sufficient force to cause the spring lever 342 to extend. In one embodiment, an outer surface of the guard 314a may come in contact with the bend 343a of the spring lever 342 and generate a second force. This second force is less than the first force, meaning the first portion 343 will not extend sufficiently to cause the switch engagement region 345 to disengage the switch 341. Alternatively, the guard 314 may not contact the spring lever 342 at all. Regardless as to whether the spring lever 342 contacts the guard 314 or is located in a void region, the pretensioned configuration of the first portion 343 has a high enough force to overcome any outward forces experienced in this configuration and thus the switch engagement region 344a engages the switch 341, thereby positioning the switch 341 in the activated configuration which causes the power source 335 to power the electronic component 333. As a result, the electronic component 333 may continue operating to sense, store, and/or transmit data as desired.

Turning to FIGS. 18-22, an alternative signal cap assembly 400 is provided. It is understood that features and/or elements which are similar to those previously described will contain similar two-digit suffixes as those previously provided and, due to similarities in function, will not be fully described for the sake of brevity. For example, the signal cap assembly includes a signal cap 430 which bears similarities to the signal cap 30 previously described. The signal cap assembly 400 includes a signal cap 430 defining a cap body and an opening, an electronic component 433 at least partially disposed in the signal cap 430, a power source 435 at least partially disposed in the signal cap 430, a switch 441 at least partially disposed in the signal cap 430, and a spring lever 442 at least partially disposed in the signal cap 430. The switch 441 is movable between an activated position and a deactivated position and causes the power source to provide power to the electronic component 433 when in the activated position.

The spring lever 442 is rotatable between a first configuration and a second configuration and includes a first component 443 forming a bend 443*a* extending radially away from the cap body and a second component 444 that slidably engages the first component via an engagement region 443*b* of the first component 443 and an engagement region 444*b* of the second component 444. The second component 444 is positioned angled relative to the first component 443 and further has a switch engagement region 444*a*. In one example, the first component 443 and the second component 444 are positioned approximately perpendicular to each other, but it is understood that the first component 443 and the second component 444 may be positioned at relative angle greater or less than 90 degrees. The second component 444 further has a pretention force applied thereto such that in a resting position, the switch engagement region 444*a* is located away from a surface of the cap body.

In one example, the spring lever 442 is rotatably coupled to the signal cap 430 by engaging an extension 436 of the tubular member 432 with a rotatable coupling 447 disposed on the first component 443. This connection maintains the spring lever 442 in the signal cap 430 while permitting rotation between a first and a second configuration. As such, the first engagement region 443*b* may move in a generally radial direction. Additionally, the second component 444 may couple to or engage the cover member 431 by wedging a portion of the second component 444 between the cover member 431 and the electronic component 433 and/or the battery 435. So configured, the second engagement region 444*b* may move in a generally axial direction. Other examples are possible.

When the spring lever 442 is rotated to the first configuration, the engagement regions 443*b*, 444*b* are in contact, thereby causing the second component 444 to be urged away from the switch 441. In other words, the switch engagement region 445 does not contact the switch 441 which is thereby positioned in a deactivated position and thus the electronic component 433 remains unpowered. When the spring lever 442 is rotated to the second configuration, the engagement region 443*b* of the first component 443 rotates away from the engagement region 444*b* of the second component to a point in which the engagement regions 443*b*, 444*b* do not contact, thereby allowing the second component 444 to move to a pretensioned state. As a result, the switch engagement region 445 contacts the switch 441 which is positioned in the activated position and thus the electronic component 433 is powered.

In this configuration, the second component 444 of the spring lever 442 is biased in a manner in which causes the switch engagement region 444*a* to engage the switch 441. The needle shield guard 418 does not create a force which urges the spring lever 442 into a particular configuration.

Figure 19:
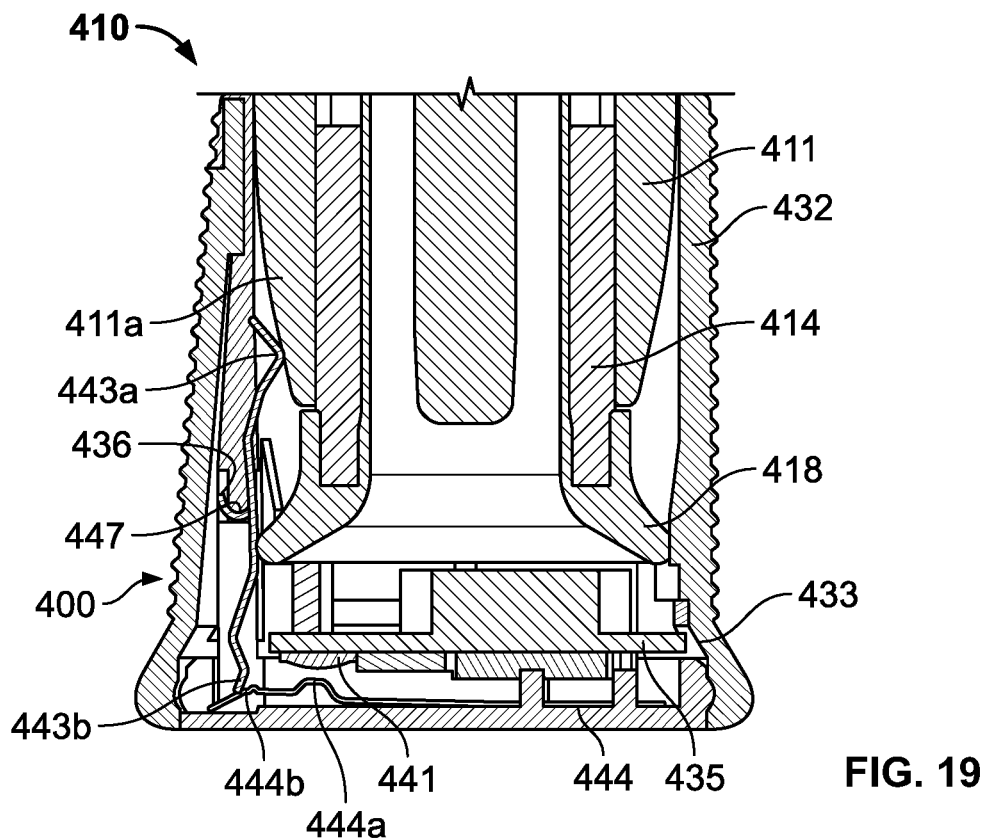
FIG. 19 comprises a cross-sectional view of a cap assembly having the spring lever of FIG. 18 disposed therein in accordance with various embodiments of the invention.

As illustrated in FIG. 19, when the device 410 is coupled to the signal cap 430, the first component 443 of the spring lever 342 contacts an outer surface 411*a* of the housing 411, thereby generating a force on the first component 443. This force exerted by the housing 411 is greater than the pretensioned force of the second component 444, and thus the spring lever 442 is forced to rotate into the first configuration in which the switch engagement region 445*a* does not engage the switch 441, thereby positioning the switch 441 in the deactivated position. As previously stated, this configuration causes the electronic component 433 to be in an unpowered state.

Figure 20A:
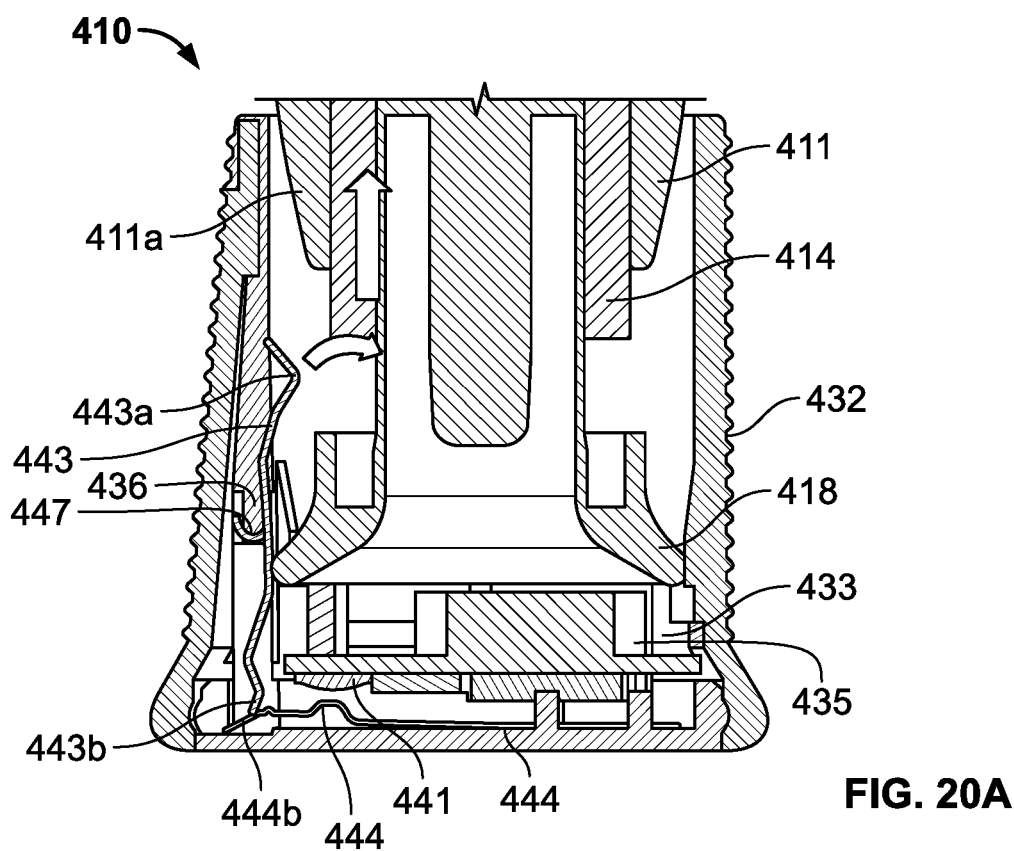
FIGS. 20A and 20B comprise cross-sectional views of the cap assembly of FIGS. 18 and 19 having the cap being removed for the purpose of administering a medication in accordance with various embodiments of the invention.
Figure 20B:
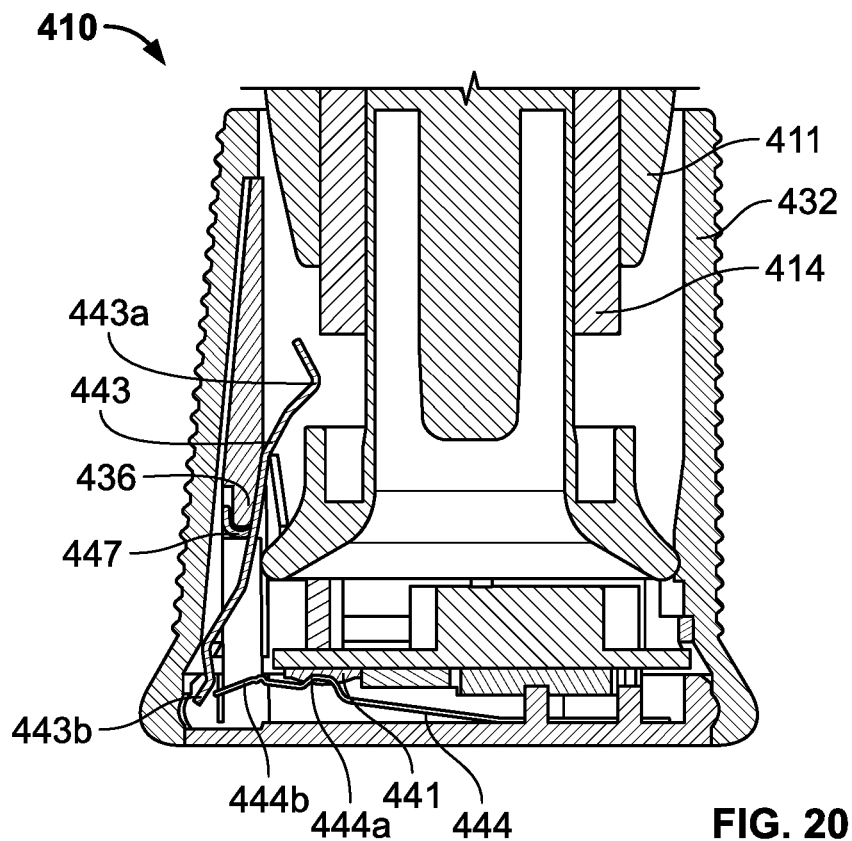

As illustrated in FIGS. 20A and 20B, the signal cap 430 is in the process of being removed from the device 410 for the purposes of administering the drug. During this process, the first component 443 of the spring lever 442 does not contact the housing 411 or any other portion of the device, and thus the second component 444 urges the first component 443 to disengage the engagement regions 443*b*, 444*b*. This disengaged configuration between the first component 443 and the second component 444 causes the switch engagement region 444*a* to engage the switch 441, thereby positioning the switch 441 in the activated configuration which causes the power source 435 to power the electronic component 433.

Figure 21A:
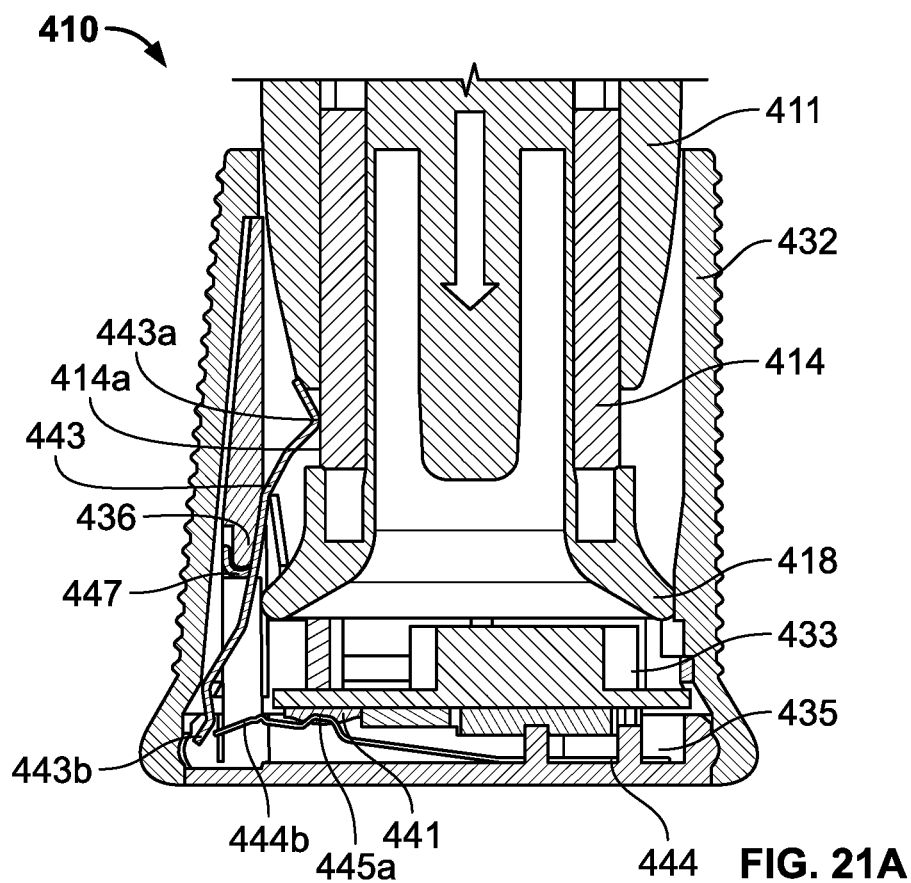
FIGS. 21A and 21B comprise cross-sectional views of the cap assembly of FIGS. 18-20 during recapping of the cap assembly to the drug delivery device prior to administering the medication in accordance with various embodiments of the invention.
Figure 21B:
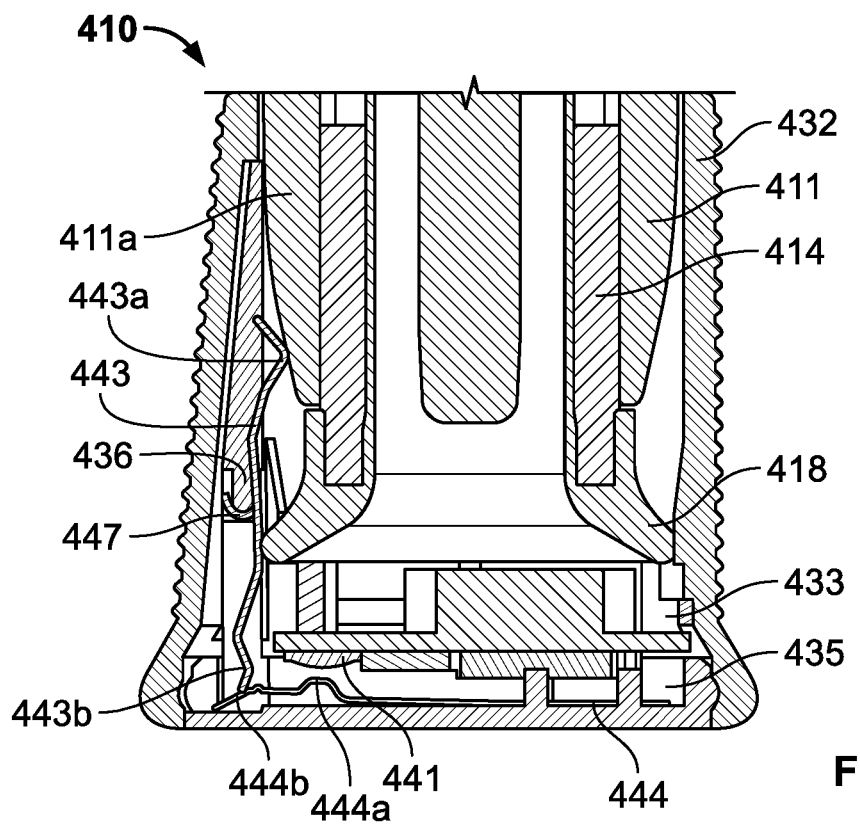
Figure 22:
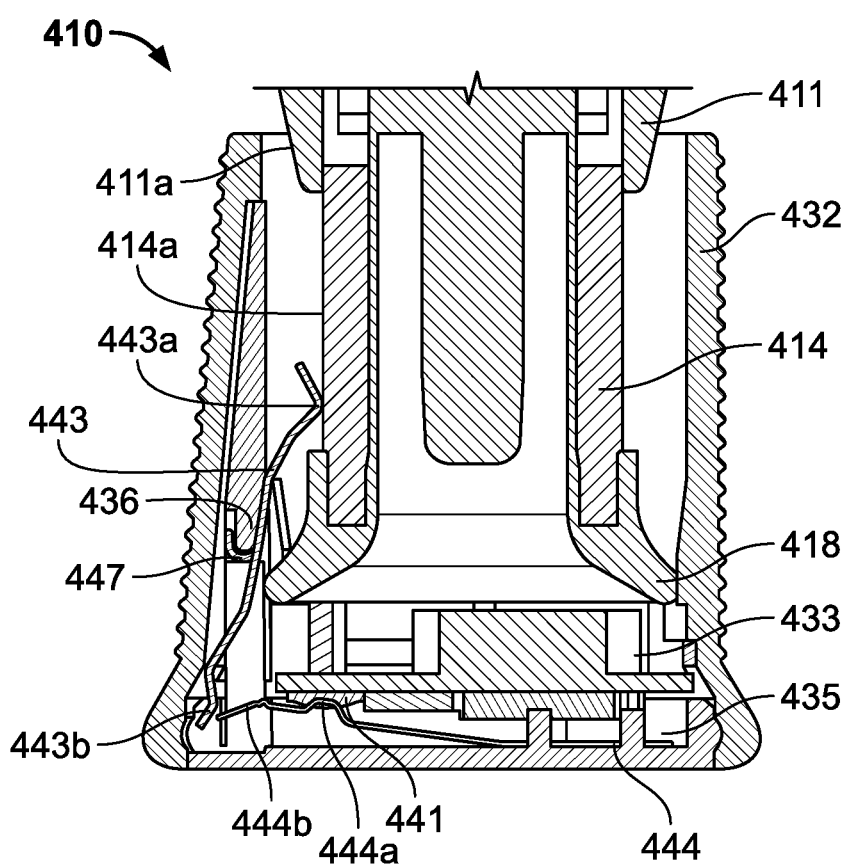
FIG. 22 comprises a cross-sectional view of the cap assembly of FIGS. 18-21 after recapping of the cap assembly to the drug delivery device after administering the medication in accordance with various embodiments of the invention.

As illustrated in FIGS. 21A and 21B, if the user decides they do not wish to administer the drug at the present time, the signal cap 430 may be recapped onto the device 410. When this occurs, the outer surface 411*a* of the housing 411 again contacts the bend 443*a* of the spring lever 442 and thereby exerts a force on the spring lever 442 causing the first component 443 to rotate so that the engagement regions 443*b*, 444*b* engage each other and forcing the switch engagement region 444*a* of the second component 444 to disengage the switch 441, thereby positioning the switch 441 in the deactivated position. As previously stated, this configuration causes the electronic component 433 to be in an unpowered state. As a result, the power source 435 is not drained and will be ready to provide power to the electronic component 433 as needed.

As illustrated in FIG. 22, the user has again removed the signal cap 430, administered the drug contained in the device 410, and returned the signal cap 430 to the device 410. As previously described, the guard 414 is now disposed in the third position. Because of the extension of the guard 414 relative to the housing 411, the outer surface 411*a* of the housing 411 is precluded from contacting the spring lever 442 in a manner which generates a sufficient force to cause the engagement regions 443*b*, 444*b* to engage each other. In one embodiment, an outer surface of the guard 414*a* may come in contact with the bend 443*a* of the spring lever 442 and generate a second force. However, the force exerted on the first component 443 is less than the pretensioned force of the second component 444, thus the spring lever 442 will remain in the engaged portion. Alternatively, the guard 414 may not contact the spring lever 442 at all. Regardless as to whether the spring lever 442 contacts the guard 414 or is located in a void region, the pretensioned force of the second component 444 is large enough to overcome any outward forces exerted on the first component 443 and thus the switch engagement region 444*a* engages the switch 441, thereby positioning the switch 441 in the activated configuration which causes the power source 435 to power the electronic component 433. As a result, the electronic component 433 may continue operating to sense, store, and/or transmit data as desired.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/Ila receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-W10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, signal cap, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed is:

1. A drug delivery device comprising:
   a housing defining a shell having a distal end;
   a drug delivery assembly at least partially disposed within the housing, the drug delivery assembly comprising a guard which engages an inner surface of the housing and is movable between at least a first position, a second position, and a third position relative to the housing, the guard adapted to at least partially restrict external contact with a cannula, wherein the distal end of the shell of the housing defines an opening through which the cannula is adapted to at least partially extend outwardly therefrom;
   a cap defining a shell and being adapted to at least partially cover the distal end of the shell of the housing;
   at least one electronic component at least partially disposed in the cap, and
   a power source at least partially disposed in the cap for selectively powering the at least one electronic component; and
   a switch assembly at least partially disposed in the cap, the switch assembly adapted to:
      cause the power source to provide power to the at least one electronic component when the cap is removed from the housing,
      restrict the power source from providing power to the at least one electronic component when the cap is coupled to the housing and the guard is in the first position, and
      cause the power source to provide power to the at least one electronic component when the cap is coupled to the housing and the guard is in the third position.

2. The drug delivery device of claim 1, the switch assembly further comprising:
   a switch being at least partially disposed in the shell of the cap and being movable between an activated position and a deactivated position, the switch being adapted to cause the power source to provide power to the at least one electronic component when in the activated position; and
   a spring lever at least partially disposed in the shell of the cap, at least a portion of the spring lever being movable between at least a first position and a second position; wherein (a) when the cap is coupled to the housing and the guard resides in the first position of the guard relative to the housing, a portion of the housing contacts the spring lever and moves the spring lever into the first position of the spring lever such that the spring lever urges the switch into the deactivated position, (b) when the cap is coupled to the housing and the guard occupies the third position relative to the housing, the spring lever resides outside of the first position of the spring lever such that the switch occupies the activated position, and (c) when the cap is removed from the housing, the spring lever is out of contact with the drug delivery assembly and occupies the second position of the spring lever such that the switch occupies the activated position.

3. The drug delivery device of claim 2, wherein when the cap is coupled to the housing and the guard occupies the third position, the spring lever is out of contact with the drug delivery assembly and occupies the second position of the spring lever such that the switch occupies the activated position.

4. The drug delivery device of claim 2, wherein the spring lever includes a rigid portion and a resilient portion.

5. The drug delivery device of claim 2, further comprising a needle shield remover coupled to the cap, the needle shield remover adapted to apply a biasing force to a resilient portion of the spring lever to urge the spring lever towards the second position of the spring lever.

6. The drug delivery device of claim 2, wherein the spring lever is rotatable and comprises a first section, a second section extending from the first section at an angle and having a first length having a switch engagement region and a second length forming a substantially U-shaped section with the first length, the second length receiving a compression force from a needle shield remover, wherein the spring lever rotates between the first position of the spring lever when the first section contacts the portion of the housing and the second position of the spring lever when the first section either contacts the guard or is disposed within a void region of the drug delivery device.

7. The drug delivery device of claim 2, wherein the spring lever comprises a first portion forming a bend extending radially away from the housing and a second portion having a switch engagement region, wherein (a) when the bend experiences a first force exerted by a first portion of the drug delivery device, the switch engagement region causes the switch to be positioned in the deactivated position, and (b) when the bend experiences a second force exerted by one of a second portion of the drug delivery device and a void region of the drug delivery device, the switch engagement region causes the switch to be positioned in the activated position.

8. The drug delivery, device of claim 2, wherein the spring lever comprises a first component forming a bend extending radially away from the cap and a second component positioned angled relative to the first component, the second component having a switch engagement region and having a pretension force applied thereto;

wherein in a first configuration, the first component contacts the second component to urge the switch engagement region away from the switch such that the switch is in the deactivated position, wherein in a second configuration, the first component does not contact the second component thereby allowing the second component to move to a pretensioned state whereby the switch engagement region engages and urges the switch to the activated position.

9. The drug delivery device of claim 1, wherein the housing defines at least one groove formed on the inner surface thereof and the guard includes at least one protrusion adapted to engage the at least one groove, wherein the first position, the second position, and the third position of the guard correspond to a first stop, a second stop, and a third stop of the at least one groove.

10. The drug delivery device of claim 9, wherein the at least one groove comprises a first section defining a first catch, a second section extending in a substantially axial direction, and a third section defining a second catch, wherein at least a portion of the first section is angled relative to the second section.

11. The drug delivery device of claim 10, wherein the drug delivery assembly further comprises a spring which exerts a force which causes the at least one protrusion to engage the first catch, wherein upon exerting a compressive force on the spring, the at least one protrusion is adapted to traverse the at least one groove until the guard reaches the second position, and upon removing the compressive force on the spring, the at least one protrusion is adapted to traverse the second section of the at least one groove and engage the second catch.

12. The drug delivery device of claim 1, wherein the guard defines at least one groove formed on an outer surface thereof and the housing includes at least one protrusion adapted to engage the at least one groove, wherein the first position, the second position, and the third position of the guard correspond to a first stop, a second stop, and a third stop of the at least one groove.

13. The drug delivery device of claim 1, wherein the at least one electronic component is adapted to generate data representative of at least one of a condition and an operational state of the drug delivery device, the at least one electronic component further being adapted to transmit the data to a processing unit.

14. The drug delivery device of claim 1, further comprising a primary container and a drug disposed in the primary container.

15. The drug delivery device of claim 14, wherein the drug comprises one of:

(a) a granulocyte colony-stimulating factor (G-CSF);

(b) a monoclonal antibody (IgG) that binds human Proprotein Convertase Subtilisin/Kexin Type 9 (PCSK9);

(c) a product that relates to calcitonin gene-related peptide (CGRP);

(d) a product that targets or modulates sclerostin;

(e) an etanercept;

(f) a TNF-receptor/Fc fusion protein;

(g) a TNF blocker; or (h) bispecific T cell engager antibodies such as blinatumomab.

* * * * *

UNITED STATES PATENT AND TRADEMARK OFFICE
CERTIFICATE OF CORRECTION

PATENT NO. : 11,351,308 B2
APPLICATION NO. : 15/775630
DATED : June 7, 2022
INVENTOR(S) : Huaying Yang et al.

It is certified that error appears in the above-identified patent and that said Letters Patent is hereby corrected as shown below:

In the Claims

Column 34, Line 40, In Claim 1 "cap, and" should be -- cap; --.

Column 35, Line 54, In Claim 8 "delivery," should be -- delivery --.

Signed and Sealed this
Twenty-ninth Day of November, 2022

Katherine Kelly Vidal
*Director of the United States Patent and Trademark Office*